(12) United States Patent
Neeley et al.

(10) Patent No.: US 11,843,904 B2
(45) Date of Patent: Dec. 12, 2023

(54) AUTOMATED COMBINED DISPLAY OF MEASUREMENT DATA

(71) Applicant: Fluke Corporation, Everett, WA (US)

(72) Inventors: John Neeley, Seattle, WA (US); Bradey Honsinger, Everett, WA (US); Tyler Bennett Evans, Edmonds, WA (US); Joseph V. Ferrante, Redmond, WA (US)

(73) Assignee: Fluke Corporation, Everett, WA (US)

( * ) Notice: Subject to any disclaimer, the term of this patent is extended or adjusted under 35 U.S.C. 154(b) by 0 days.

(21) Appl. No.: 17/074,470

(22) Filed: Oct. 19, 2020

(65) Prior Publication Data

US 2021/0033497 A1  Feb. 4, 2021

Related U.S. Application Data

(63) Continuation of application No. 14/214,662, filed on Mar. 15, 2014, now Pat. No. 10,809,159.
(Continued)

(51) Int. Cl.
*H04Q 9/00* (2006.01)
*G01M 99/00* (2011.01)
(Continued)

(52) U.S. Cl.
CPC .......... *H04Q 9/00* (2013.01); *G01D 1/00* (2013.01); *G01D 7/00* (2013.01); *G01D 7/02* (2013.01);
(Continued)

(58) Field of Classification Search
CPC .... G01M 99/00; G06T 11/206; H04N 5/2322; H04N 5/23; H04N 5/23229; H04N 5/33;
(Continued)

(56) References Cited

U.S. PATENT DOCUMENTS 4,644,320 A   2/1987 Carr et al.
4,717,872 A   1/1988 Wagner et al.
(Continued)

FOREIGN PATENT DOCUMENTS

CA   2152024 A1   12/1995
CN   1237302 A    12/1999
(Continued)

OTHER PUBLICATIONS

Bicelli et al., "From the Traditional Multimeter to the Wireless Multimeter Networking", IMTC 2006—Instrumentation and Measurement Technology Conference, Sorrento, Italy, Apr. 24-27, 2006, pp. 1581-1586.
(Continued)

*Primary Examiner* — Charles L Beard
(74) *Attorney, Agent, or Firm* — SEED INTELLECTUAL PROPERTY LAW GROUP LLP

(57) ABSTRACT

A computer-implemented method, system, and computer-readable medium for automatically generating a combined display of measurement data representing a combined measurement, such as a multiphase parameter, includes establishing, by a mobile computing device, communication connections with a plurality of measurement devices configured to generate measurement data. The mobile computing device receives the measurement data generated by the plurality of measurement devices, and in response to information indicative of the measurement data representing related parts of a combined measurement, the mobile computing device automatically groups the measurement data received from the measurement devices and automatically displays the grouped measurement data in a combined display that shares at least one axis of measurement. In at least one embodiment, the combined measurement is a multiphase parameter, such as a three-phase electrical
(Continued)

parameter, and the combined display is a graph in which the measurement data shares at least one axis of measurement, such as time.

20 Claims, 6 Drawing Sheets

Related U.S. Application Data

(60) Provisional application No. 61/876,719, filed on Sep. 11, 2013, provisional application No. 61/801,380, filed on Mar. 15, 2013.

(51) Int. Cl.

| | | |
|---|---|---|
| G06F 15/00 | (2006.01) | |
| G08B 5/00 | (2006.01) | |
| G01D 7/02 | (2006.01) | |
| G16H 10/40 | (2018.01) | |
| H04N 23/80 | (2023.01) | |
| G06V 10/75 | (2022.01) | |
| G06T 11/20 | (2006.01) | |
| H04N 5/33 | (2023.01) | |
| G01D 1/00 | (2006.01) | |
| G01D 7/00 | (2006.01) | |
| G01D 9/00 | (2006.01) | |
| G06Q 20/08 | (2012.01) | |
| G08C 17/02 | (2006.01) | |
| G01D 7/08 | (2006.01) | |

(52) U.S. Cl.
CPC ............ *G01D 7/08* (2013.01); *G01D 9/00* (2013.01); *G01M 99/00* (2013.01); *G06F 15/00* (2013.01); *G06Q 20/085* (2013.01); *G06Q 20/0855* (2013.01); *G06T 11/206* (2013.01); *G06V 10/75* (2022.01); *G08B 5/00* (2013.01); *G08C 17/02* (2013.01); *G16H 10/40* (2018.01); *H04N 5/33* (2013.01); *H04N 23/80* (2023.01); *H04Q 2209/40* (2013.01); *H04Q 2209/47* (2013.01); *H04Q 2209/50* (2013.01); *H04Q 2209/86* (2013.01); *H04Q 2209/883* (2013.01)

(58) Field of Classification Search
CPC ...... H04N 23/80; H04Q 9/00; H04Q 2209/40; H04Q 2209/47; H04Q 2209/50; H04Q 2209/86; H04Q 2209/883; G08C 17/02; G08B 5/00; G06Q 20/085; G06Q 20/0855; G06K 9/64; G06F 15/00; G01D 1/00; G01D 7/00; G01D 7/02; G01D 7/08; G01D 9/00; G16H 10/40; G06V 10/75
See application file for complete search history.

(56) References Cited

U.S. PATENT DOCUMENTS

| | | | |
|---|---|---|---|
| 4,754,218 A | 6/1988 | Wagner et al. | |
| 5,146,371 A * | 9/1992 | Hamada | G01D 9/00 |
| | | | 360/32 |
| 5,172,052 A | 12/1992 | Wells | |
| 5,371,842 A * | 12/1994 | Easton | G01R 13/0227 |
| | | | 345/442 |
| 5,386,117 A | 1/1995 | Piety et al. | |
| 5,428,342 A | 6/1995 | Enoki et al. | |
| 5,493,287 A * | 2/1996 | Bane | G08C 17/02 |
| | | | 340/870.03 |
| 5,594,332 A | 1/1997 | Harman et al. | |
| 5,637,871 A | 6/1997 | Piety et al. | |
| 5,650,771 A | 7/1997 | Lee | |
| 5,664,207 A | 9/1997 | Crumpler et al. | |
| 5,748,104 A | 5/1998 | Argyroudis et al. | |
| 5,767,667 A | 6/1998 | Shafie | |
| 5,992,237 A | 11/1999 | McCarty et al. | |
| 6,122,603 A | 9/2000 | Budike, Jr. | |
| 6,184,798 B1 * | 2/2001 | Egri | G08C 17/02 |
| | | | 340/870.1 |
| 6,195,018 B1 * | 2/2001 | Ragle | G08C 15/06 |
| | | | 340/870.11 |
| 6,202,491 B1 | 3/2001 | McCarty et al. | |
| 6,219,340 B1 * | 4/2001 | Cutler | H04W 52/362 |
| | | | 370/241 |
| 6,229,526 B1 | 5/2001 | Berstis | |
| 6,243,105 B1 * | 6/2001 | Hoyer | G06T 11/206 |
| | | | 345/418 |
| 6,261,230 B1 * | 7/2001 | Bardy | G16H 40/67 |
| | | | 600/300 |
| 6,280,380 B1 * | 8/2001 | Bardy | G16H 20/70 |
| | | | 600/300 |
| 6,298,308 B1 | 10/2001 | Reid et al. | |
| 6,336,900 B1 | 1/2002 | Alleckson et al. | |
| 6,363,057 B1 | 3/2002 | Ardalan et al. | |
| 6,363,488 B1 | 3/2002 | Ginter et al. | |
| 6,437,692 B1 | 8/2002 | Petite et al. | |
| 6,441,723 B1 | 8/2002 | Mansfield, Jr. et al. | |
| 6,489,884 B1 | 12/2002 | Lamberson et al. | |
| 6,496,705 B1 * | 12/2002 | Ng | A61B 5/0006 |
| | | | 455/502 |
| 6,501,983 B1 | 12/2002 | Natarajan et al. | |
| 6,502,063 B1 * | 12/2002 | Eriksson | G01D 1/00 |
| | | | 375/346 |
| 6,538,577 B1 * | 3/2003 | Ehrke | H04Q 9/00 |
| | | | 340/637 |
| 6,571,140 B1 | 5/2003 | Wewalaarachchi et al. | |
| 6,684,245 B1 | 1/2004 | Shuey et al. | |
| 6,826,514 B1 * | 11/2004 | Antico | H04B 7/18573 |
| | | | 702/187 |
| 6,862,540 B1 * | 3/2005 | Welch | G01F 15/063 |
| | | | 340/870.02 |
| 6,885,309 B1 * | 4/2005 | Van Heteren | G08C 15/06 |
| | | | 340/870.11 |
| 6,891,478 B2 | 5/2005 | Gardner | |
| 6,934,862 B2 | 8/2005 | Sharood et al. | |
| 6,956,500 B1 | 10/2005 | Ducharme et al. | |
| 6,985,819 B2 | 1/2006 | Lipscomb et al. | |
| 6,993,417 B2 | 1/2006 | Osann, Jr. | |
| 7,076,239 B2 | 7/2006 | Kirkup et al. | |
| 7,130,844 B2 * | 10/2006 | Elder | G06F 16/3328 |
| 7,149,285 B2 * | 12/2006 | Kennedy | H04M 3/301 |
| | | | 379/27.01 |
| 7,191,184 B2 | 3/2007 | Laborde et al. | |
| 7,236,900 B2 * | 6/2007 | Hagen | G01R 13/206 |
| | | | 324/76.22 |
| 7,289,887 B2 | 10/2007 | Rodgers | |
| 7,304,618 B2 * | 12/2007 | Plathe | G01R 1/04 |
| | | | 324/111 |
| 7,310,583 B2 | 12/2007 | De La Quintana | |
| 7,312,603 B2 | 12/2007 | Luo et al. | |
| 7,317,404 B2 | 1/2008 | Cumeralto et al. | |
| 7,327,228 B2 * | 2/2008 | Min | G06F 8/60 |
| | | | 180/167 |
| 7,338,443 B1 * | 3/2008 | Tucker | G16H 40/20 |
| | | | 128/920 |
| 7,382,247 B2 | 6/2008 | Welch et al. | |
| 7,385,524 B1 | 6/2008 | Orlosky | |
| 7,423,985 B1 | 9/2008 | Hill | |
| 7,424,527 B2 | 9/2008 | Petite | |
| 7,454,050 B2 | 11/2008 | Garvey | |
| 7,478,305 B2 | 1/2009 | Betawar et al. | |
| 7,480,501 B2 | 1/2009 | Petite | |
| 7,528,372 B2 | 5/2009 | Garvey, III et al. | |
| 7,535,378 B2 * | 5/2009 | Cornwall | H04Q 9/00 |
| | | | 340/12.54 |
| 7,541,941 B2 | 6/2009 | Bogolea et al. | |
| 7,561,200 B2 | 7/2009 | Garvey, III et al. | |
| 7,561,867 B2 | 7/2009 | Frye, Jr. | |
| 7,616,110 B2 | 11/2009 | Crump et al. | |

(56) References Cited

U.S. PATENT DOCUMENTS

| | | |
|---|---|---|
| 7,703,032 B2 | 4/2010 | Wells |
| 7,706,596 B2 | 4/2010 | Garvey |
| 7,728,275 B2 | 6/2010 | Blanchard |
| 7,746,092 B2 | 6/2010 | Li |
| 7,791,351 B2 | 9/2010 | Raber |
| 7,813,822 B1 | 10/2010 | Hoffberg |
| 7,848,905 B2 | 12/2010 | Troxler et al. |
| 7,902,507 B1 | 3/2011 | Garvey, III et al. |
| 7,907,995 B2 * | 3/2011 | Nagata .................. A61B 5/742 |
| | | 600/523 |
| 7,917,382 B2 | 3/2011 | Cereghini et al. |
| 7,960,965 B2 | 6/2011 | Lund |
| 7,995,830 B2 | 8/2011 | Garvey |
| 8,003,942 B2 | 8/2011 | Garvey, III et al. |
| 8,005,576 B2 | 8/2011 | Rodgers |
| 8,024,724 B2 | 9/2011 | Garrison Stuber et al. |
| 8,036,597 B2 | 10/2011 | Rahman et al. |
| 8,085,143 B2 | 12/2011 | Hollander et al. |
| 8,090,480 B2 | 1/2012 | Brumfield et al. |
| 8,094,034 B2 | 1/2012 | Patel et al. |
| 8,119,986 B1 | 2/2012 | Garvey, III et al. |
| 8,124,923 B2 | 2/2012 | Blanchard |
| 8,131,489 B2 * | 3/2012 | Heuser .................. G01R 13/02 |
| | | 702/67 |
| 8,148,687 B1 | 4/2012 | Praly |
| 8,170,722 B1 | 5/2012 | Elberbaum |
| 8,233,486 B2 | 7/2012 | Phuah et al. |
| 8,269,650 B2 | 9/2012 | Cornwall et al. |
| 8,300,922 B1 | 10/2012 | Garvey, III |
| 8,319,658 B2 * | 11/2012 | Conant .................. G06Q 10/10 |
| | | 340/870.01 |
| 8,334,513 B1 | 12/2012 | Garvey, III et al. |
| 8,339,093 B2 * | 12/2012 | Lu .......................... H02P 23/00 |
| | | 318/807 |
| 8,358,903 B1 | 1/2013 | Meads et al. |
| 8,368,001 B2 | 2/2013 | Blanchard |
| 8,410,931 B2 | 4/2013 | Petite et al. |
| 8,427,006 B2 | 4/2013 | Gilbert |
| 8,432,154 B2 | 4/2013 | Lund |
| 8,447,541 B2 * | 5/2013 | Rada ..................... G01D 4/004 |
| | | 62/130 |
| 8,450,995 B2 | 5/2013 | Wagner |
| 8,456,278 B1 | 6/2013 | Bergman et al. |
| 8,489,063 B2 | 7/2013 | Petite |
| 8,502,821 B2 * | 8/2013 | Louise ............... G01R 13/0236 |
| | | 345/440 |
| 8,576,231 B2 * | 11/2013 | Woodings ............. G06T 11/206 |
| | | 345/440 |
| 8,581,743 B2 | 11/2013 | Chan et al. |
| 8,618,930 B2 | 12/2013 | Papadopoulos et al. |
| 8,639,465 B1 | 1/2014 | Elberbaum |
| 8,643,539 B2 | 2/2014 | Pauly et al. |
| 8,665,082 B2 | 3/2014 | Glenn et al. |
| 8,707,193 B2 | 4/2014 | Khazanov et al. |
| 8,712,732 B2 * | 4/2014 | Patel .................. G01R 19/2513 |
| | | 702/190 |
| 8,738,925 B1 * | 5/2014 | Park ........................ H04B 7/26 |
| | | 713/186 |
| 8,754,779 B2 * | 6/2014 | Ruther ................. G07C 5/0816 |
| | | 340/870.02 |
| 8,836,318 B2 | 9/2014 | Cheng et al. |
| 8,870,086 B2 | 10/2014 | Tessier et al. |
| 8,880,092 B1 * | 11/2014 | Cooley ................. H04W 64/00 |
| | | 455/115.2 |
| 8,884,553 B2 | 11/2014 | Hai |
| 8,902,249 B1 | 12/2014 | Wilson et al. |
| 8,976,039 B2 | 3/2015 | O'Hara et al. |
| 8,983,785 B2 * | 3/2015 | Panko ................... G01R 13/029 |
| | | 702/67 |
| 9,076,275 B2 | 7/2015 | Chinnadurai et al. |
| 9,081,829 B2 * | 7/2015 | Bhave ..................... H04L 43/04 |
| 9,117,251 B2 | 8/2015 | Schmidt et al. |
| 9,151,818 B2 | 10/2015 | Danesh et al. |
| 9,172,275 B2 | 10/2015 | Bhakta |
| 9,191,286 B2 * | 11/2015 | Lachapelle ........... H04L 41/145 |
| 9,197,949 B2 | 11/2015 | Indovina et al. |
| 9,250,275 B2 | 2/2016 | Patel et al. |
| 9,319,288 B2 | 4/2016 | Somaiya et al. |
| 9,347,796 B1 * | 5/2016 | Rapadas ................ G01D 4/002 |
| 9,363,148 B2 | 6/2016 | Somaiya et al. |
| 9,384,116 B2 | 7/2016 | Rider et al. |
| 9,408,250 B2 | 8/2016 | Yi et al. |
| 9,430,353 B2 | 8/2016 | Shafi |
| 9,430,558 B2 | 8/2016 | Bhat et al. |
| 9,438,300 B1 | 9/2016 | Oliaei |
| 9,449,408 B2 | 9/2016 | Benson et al. |
| 9,454,820 B1 | 9/2016 | Kirmani et al. |
| 9,467,745 B1 * | 10/2016 | Hotchkiss .............. H04N 21/25 |
| 9,477,784 B1 | 10/2016 | Bhave et al. |
| 9,489,745 B1 | 11/2016 | Heitz, III et al. |
| 9,495,187 B2 | 11/2016 | Bingham et al. |
| 9,501,555 B2 | 11/2016 | Zhou et al. |
| 9,501,849 B2 | 11/2016 | Wong et al. |
| 9,541,472 B2 | 1/2017 | Neeley et al. |
| 9,557,720 B1 * | 1/2017 | Woods .................. G01R 31/085 |
| 9,563,218 B2 * | 2/2017 | Hall ......................... H02J 3/00 |
| 9,564,945 B1 * | 2/2017 | Goyal .................... H04B 3/462 |
| 9,704,369 B2 | 7/2017 | Richardson et al. |
| 9,733,974 B2 | 8/2017 | Bingham et al. |
| 9,753,935 B1 * | 9/2017 | Tobin ................ G06F 16/24568 |
| 9,766,270 B2 * | 9/2017 | Heydron ................ G01R 15/12 |
| 9,773,330 B1 | 9/2017 | Douglas et al. |
| 9,778,285 B2 * | 10/2017 | Fox ..................... G01R 1/06788 |
| 9,792,020 B1 * | 10/2017 | Kelley ................ G06Q 10/0639 |
| 9,864,383 B2 | 1/2018 | Reider et al. |
| 9,866,026 B2 * | 1/2018 | Nomura ................... H02J 7/35 |
| 9,887,541 B2 * | 2/2018 | Hall .................. H02J 13/00026 |
| 9,900,560 B1 | 2/2018 | Kirmani et al. |
| 9,946,288 B2 | 4/2018 | Sato et al. |
| 9,955,527 B2 * | 4/2018 | Uchida ................... H04W 88/16 |
| 9,995,655 B2 | 6/2018 | Dagnino et al. |
| 10,019,890 B2 | 7/2018 | Tanaka |
| 10,054,464 B2 | 8/2018 | Quady |
| 10,067,038 B2 * | 9/2018 | Hou ........................ F04B 51/00 |
| 10,088,389 B2 | 10/2018 | Neeley et al. |
| 10,095,659 B2 | 10/2018 | Katz et al. |
| 10,120,021 B1 * | 11/2018 | Silva ....................... G01R 21/02 |
| 10,128,937 B2 | 11/2018 | Yamazaki |
| 10,129,611 B2 * | 11/2018 | Primm ..................... H04Q 9/00 |
| 10,209,271 B2 * | 2/2019 | Epperson ................ G01R 1/025 |
| 10,216,695 B1 | 2/2019 | Shankar et al. |
| 10,312,681 B2 * | 6/2019 | Aiello ....................... H02J 3/12 |
| 10,337,946 B1 * | 7/2019 | Tan ........................ G06F 16/29 |
| 10,417,224 B2 * | 9/2019 | Duffield ................. G06F 16/245 |
| 10,453,573 B2 | 10/2019 | Greene et al. |
| 10,509,061 B2 * | 12/2019 | Brown ..................... G01D 3/08 |
| 10,530,666 B2 * | 1/2020 | Venkitapathi .......... H04L 43/045 |
| 10,540,053 B2 * | 1/2020 | Gasperi ................. G06F 16/972 |
| 10,555,057 B2 * | 2/2020 | Koezuka .................. H04Q 9/00 |
| 10,571,493 B2 * | 2/2020 | Sonderegger ........ G01R 19/003 |
| 10,614,132 B2 * | 4/2020 | Bingham ............ G06F 16/90335 |
| 10,628,442 B1 * | 4/2020 | Naskar .................. G06F 16/248 |
| 10,666,048 B2 * | 5/2020 | Hall .................. H02J 13/00026 |
| 10,734,838 B2 * | 8/2020 | Roytelman ............... H02J 3/00 |
| 10,748,406 B2 * | 8/2020 | Boerhout ................ G08B 21/18 |
| 10,812,957 B2 * | 10/2020 | Wallington ........... H04W 8/005 |
| 10,908,188 B2 * | 2/2021 | Laurino ................... G01R 1/04 |
| 10,998,709 B1 * | 5/2021 | Wulfekuhle ............. H02H 3/202 |
| 11,190,017 B1 * | 11/2021 | Rothschild ............... H02J 3/381 |
| 2001/0001850 A1 * | 5/2001 | Miller .................... G01R 23/16 |
| | | 702/67 |
| 2001/0025138 A1 * | 9/2001 | Bardy .................... A61B 5/7465 |
| | | 600/300 |
| 2001/0038343 A1 * | 11/2001 | Meyer ...................... H04Q 9/00 |
| | | 340/870.02 |
| 2001/0051764 A1 * | 12/2001 | Bardy .................... A61N 1/37258 |
| | | 600/300 |
| 2002/0190208 A1 * | 12/2002 | Wood ..................... H04N 25/63 |
| | | 348/E5.081 |
| 2002/0193144 A1 | 12/2002 | Belski et al. |
| 2003/0020759 A1 * | 1/2003 | Cancilla ................... G01D 1/00 |
| | | 715/810 |
| 2003/0050737 A1 | 3/2003 | Osann, Jr. |

(56) References Cited

U.S. PATENT DOCUMENTS

| | | |
|---|---|---|
| 2003/0058243 A1* | 3/2003 | Faust .................... G06T 11/206 345/440 |
| 2003/0128212 A1 | 7/2003 | Pitkow |
| 2003/0135338 A1* | 7/2003 | Knaus .................... G01D 4/008 702/61 |
| 2003/0158677 A1 | 8/2003 | Swarztrauber et al. |
| 2003/0216971 A1 | 11/2003 | Sick et al. |
| 2004/0028023 A1 | 2/2004 | Mandhyan et al. |
| 2004/0032433 A1* | 2/2004 | Kodosky ............ G06F 3/04817 715/810 |
| 2004/0034496 A1* | 2/2004 | Correll .................. G06T 11/206 702/127 |
| 2004/0061623 A1* | 4/2004 | Tootoonian Mashhad .................. G01D 4/008 340/870.02 |
| 2004/0066309 A1* | 4/2004 | Jang ........................ H04Q 9/00 340/870.02 |
| 2004/0113810 A1* | 6/2004 | Mason, Jr. .............. H04Q 9/00 709/200 |
| 2004/0140908 A1 | 7/2004 | Gladwin et al. |
| 2004/0197040 A1 | 10/2004 | Walker et al. |
| 2004/0227501 A1 | 11/2004 | Wobben |
| 2004/0249605 A1 | 12/2004 | Komatsu |
| 2004/0253997 A1 | 12/2004 | Kochie |
| 2005/0060107 A1 | 3/2005 | Rodenberg, III et al. |
| 2005/0065743 A1* | 3/2005 | Cumming .............. G01R 22/10 702/62 |
| 2005/0125512 A1 | 6/2005 | Fuller, III et al. |
| 2005/0132241 A1 | 6/2005 | Curt et al. |
| 2005/0171411 A1* | 8/2005 | KenKnight ............ G16H 10/60 600/300 |
| 2005/0184882 A1* | 8/2005 | Angelis .................. H04Q 9/00 340/870.02 |
| 2005/0194962 A1 | 9/2005 | Briese et al. |
| 2005/0195757 A1 | 9/2005 | Kidder et al. |
| 2005/0212526 A1 | 9/2005 | Blades |
| 2005/0225347 A1 | 10/2005 | Khandros et al. |
| 2005/0237221 A1* | 10/2005 | Brian ...................... H04Q 9/00 340/870.02 |
| 2005/0240540 A1* | 10/2005 | Borleske ................ G06Q 30/04 705/401 |
| 2005/0270151 A1 | 12/2005 | Winick |
| 2005/0278007 A1 | 12/2005 | Godara |
| 2005/0289264 A1 | 12/2005 | Illowsky et al. |
| 2006/0022663 A1* | 2/2006 | Chen ........................ H04Q 9/00 324/142 |
| 2006/0062190 A1* | 3/2006 | Suga ...................... H04W 28/18 370/338 |
| 2006/0071812 A1* | 4/2006 | Mason .................... H04Q 9/00 340/870.02 |
| 2006/0097713 A1 | 5/2006 | Brandt |
| 2006/0101311 A1* | 5/2006 | Lipscomb .............. G07C 5/008 714/47.1 |
| 2006/0136825 A1 | 6/2006 | Cory et al. |
| 2006/0145890 A1 | 7/2006 | Junker et al. |
| 2006/0167638 A1 | 7/2006 | Murphy et al. |
| 2006/0189871 A1 | 8/2006 | Al-Ali et al. |
| 2006/0202816 A1 | 9/2006 | Crump et al. |
| 2006/0217936 A1* | 9/2006 | Mason .................. H04L 67/125 702/188 |
| 2006/0256786 A1 | 11/2006 | Bibr et al. |
| 2007/0001868 A1* | 1/2007 | Boaz ...................... G01D 4/004 340/870.02 |
| 2007/0007968 A1 | 1/2007 | Mauney, Jr. et al. |
| 2007/0013547 A1* | 1/2007 | Boaz ........................ H04Q 9/00 340/870.02 |
| 2007/0038591 A1 | 2/2007 | Haub et al. |
| 2007/0057814 A1 | 3/2007 | Goldberg et al. |
| 2007/0067360 A1* | 3/2007 | Engel ........................ H04Q 9/00 |
| 2007/0083307 A1* | 4/2007 | Pasztor .............. F02D 41/1495 701/29.2 |
| 2007/0100520 A1* | 5/2007 | Shah ...................... G07C 5/008 701/31.4 |
| 2007/0100666 A1 | 5/2007 | Stivoric et al. |
| 2007/0118310 A1* | 5/2007 | Kindseth ............ G01R 19/2513 702/64 |
| 2007/0118323 A1 | 5/2007 | Ishizuka |
| 2007/0126731 A1 | 6/2007 | Sabram |
| 2007/0127833 A1 | 6/2007 | Singh |
| 2007/0156313 A1* | 7/2007 | Fudali .................... G07C 5/008 701/31.4 |
| 2007/0156373 A1 | 7/2007 | Yamashita et al. |
| 2007/0176933 A1 | 8/2007 | Culpi et al. |
| 2007/0179754 A1 | 8/2007 | Sper |
| 2007/0182584 A1* | 8/2007 | Ogino ...................... H04Q 9/00 340/870.21 |
| 2007/0198222 A1 | 8/2007 | Schuster et al. |
| 2007/0244668 A1* | 10/2007 | Huck ...................... G01D 1/00 702/33 |
| 2007/0297112 A1 | 12/2007 | Gilbert |
| 2008/0012701 A1* | 1/2008 | Kass ...................... A61B 5/165 340/539.11 |
| 2008/0036466 A1 | 2/2008 | Raber |
| 2008/0042641 A1 | 2/2008 | Stockman |
| 2008/0046387 A1 | 2/2008 | Gopal et al. |
| 2008/0046414 A1 | 2/2008 | Haub et al. |
| 2008/0046457 A1 | 2/2008 | Haub et al. |
| 2008/0046838 A1 | 2/2008 | Haub et al. |
| 2008/0052017 A1 | 2/2008 | Smith et al. |
| 2008/0066217 A1 | 3/2008 | Van Wyk et al. |
| 2008/0068994 A1 | 3/2008 | Garrison Stuber et al. |
| 2008/0077336 A1 | 3/2008 | Fernandes |
| 2008/0082278 A1* | 4/2008 | Tan .................... G01R 13/0254 702/76 |
| 2008/0091345 A1 | 4/2008 | Patel et al. |
| 2008/0148877 A1 | 6/2008 | Sim |
| 2008/0161957 A1 | 7/2008 | Rice et al. |
| 2008/0224892 A1 | 9/2008 | Bogolea et al. |
| 2008/0231719 A1 | 9/2008 | Benson et al. |
| 2008/0269932 A1 | 10/2008 | Chardon et al. |
| 2009/0017816 A1* | 1/2009 | Chainer .............. H05K 7/20836 455/425 |
| 2009/0031042 A1 | 1/2009 | Phatak |
| 2009/0045804 A1 | 2/2009 | Durling et al. |
| 2009/0054743 A1 | 2/2009 | Stewart |
| 2009/0072985 A1 | 3/2009 | Patel et al. |
| 2009/0088991 A1 | 4/2009 | Brzezowski et al. |
| 2009/0109021 A1* | 4/2009 | Paoletti ................ G01R 31/343 702/184 |
| 2009/0128124 A1* | 5/2009 | Garland .............. G01R 15/125 324/115 |
| 2009/0128127 A1* | 5/2009 | Garland .............. G01R 19/2509 324/115 |
| 2009/0128128 A1* | 5/2009 | Garland .............. G01R 15/125 324/115 |
| 2009/0135836 A1 | 5/2009 | Veillette |
| 2009/0141593 A1 | 6/2009 | Taha |
| 2009/0150509 A1 | 6/2009 | Chang et al. |
| 2009/0174603 A1* | 7/2009 | Scalisi .................. G01C 21/165 342/450 |
| 2009/0210814 A1 | 8/2009 | Agrusa et al. |
| 2009/0225229 A1 | 9/2009 | Kobota |
| 2009/0228448 A1* | 9/2009 | Ivanov .................... G16H 40/67 |
| 2009/0237404 A1* | 9/2009 | Cannon, III .......... G06T 11/206 345/440 |
| 2009/0262138 A1 | 10/2009 | Bradbury et al. |
| 2009/0275805 A1 | 11/2009 | Lane et al. |
| 2009/0281679 A1* | 11/2009 | Taft ........................ G01D 4/004 700/297 |
| 2009/0292486 A1* | 11/2009 | Van Gorp .............. G01R 22/063 702/60 |
| 2009/0299940 A1* | 12/2009 | Hayes .................... G06N 5/025 706/47 |
| 2009/0315725 A1 | 12/2009 | Hollander et al. |
| 2009/0326410 A1* | 12/2009 | James .................... G16H 40/67 600/551 |
| 2009/0326731 A1* | 12/2009 | Bowdry ................ G01D 4/004 700/297 |
| 2010/0005331 A1 | 1/2010 | Somasundaram et al. |

(56) References Cited

U.S. PATENT DOCUMENTS

| | | |
|---|---|---|
| 2010/0014746 A1* | 1/2010 | Warnke .................. G01N 25/72 382/141 |
| 2010/0030289 A1 | 2/2010 | Casavant et al. |
| 2010/0058222 A1* | 3/2010 | Bergstrom .............. G06T 19/00 715/782 |
| 2010/0063785 A1 | 3/2010 | Pich et al. |
| 2010/0102926 A1 | 4/2010 | Grieve et al. |
| 2010/0109842 A1 | 5/2010 | Patel et al. |
| 2010/0167659 A1* | 7/2010 | Wagner .................. G08C 19/02 455/343.1 |
| 2010/0174419 A1* | 7/2010 | Brumfield .............. G01R 22/10 700/295 |
| 2010/0179438 A1 | 7/2010 | Heneghan et al. |
| 2010/0214299 A1 | 8/2010 | Robertson et al. |
| 2010/0217099 A1 | 8/2010 | LeBoeuf et al. |
| 2010/0217418 A1 | 8/2010 | Fontanot |
| 2010/0218305 A1 | 9/2010 | Weston et al. |
| 2010/0244868 A1 | 9/2010 | Cantave et al. |
| 2010/0256456 A1 | 10/2010 | Natarajan |
| 2010/0286840 A1* | 11/2010 | Powell .............. H02J 13/00002 700/295 |
| 2010/0299284 A1 | 11/2010 | Gristina et al. |
| 2010/0305889 A1* | 12/2010 | Tomlinson, Jr. ......... G06N 7/01 702/62 |
| 2010/0323555 A1* | 12/2010 | Geiger .................. G01R 11/04 439/517 |
| 2010/0329174 A1* | 12/2010 | Shuey .................. H04W 84/18 370/315 |
| 2010/0331651 A1 | 12/2010 | Groll |
| 2011/0012587 A1 | 1/2011 | Greenberg |
| 2011/0012743 A1* | 1/2011 | Van Gorp .............. G08C 17/02 340/686.6 |
| 2011/0016120 A1* | 1/2011 | Haughay, Jr. ...... A63B 71/0622 707/734 |
| 2011/0016517 A1* | 1/2011 | Kasahara .............. G01D 4/002 726/7 |
| 2011/0039571 A1* | 2/2011 | Bodine ................ H04W 24/08 455/456.1 |
| 2011/0074598 A1* | 3/2011 | Cornwall .............. G01D 4/004 340/870.01 |
| 2011/0085461 A1* | 4/2011 | Liu ........................ H04L 43/12 370/252 |
| 2011/0087461 A1 | 4/2011 | Hollander et al. |
| 2011/0099424 A1 | 4/2011 | Rivera Trevino et al. |
| 2011/0101956 A1 | 5/2011 | Thorn |
| 2011/0106589 A1* | 5/2011 | Blomberg .............. G06T 11/206 705/347 |
| 2011/0115640 A1 | 5/2011 | Jiang et al. |
| 2011/0126142 A1* | 5/2011 | Zhou .................. G05B 19/4183 715/771 |
| 2011/0137678 A1 | 6/2011 | Williams |
| 2011/0153236 A1 | 6/2011 | Montreuil et al. |
| 2011/0184267 A1* | 7/2011 | Duke ..................... A61B 5/725 600/365 |
| 2011/0199916 A1* | 8/2011 | Garrett ................ H04W 64/003 370/252 |
| 2011/0200045 A1 | 8/2011 | Baehre |
| 2011/0212700 A1 | 9/2011 | Petite |
| 2011/0243005 A1 | 10/2011 | Sun |
| 2011/0248857 A1 | 10/2011 | Rutherford et al. |
| 2011/0251807 A1 | 10/2011 | Rada et al. |
| 2011/0270797 A1* | 11/2011 | Adams .................... G06N 7/00 706/59 |
| 2011/0285546 A1 | 11/2011 | Vadali |
| 2011/0288810 A1 | 11/2011 | Ishikawa et al. |
| 2011/0288900 A1 | 11/2011 | McQueen et al. |
| 2011/0298301 A1 | 12/2011 | Wong et al. |
| 2011/0307418 A1* | 12/2011 | Bouzaglo .............. G01D 4/002 705/412 |
| 2011/0309820 A1 | 12/2011 | Khanke et al. |
| 2011/0316717 A1 | 12/2011 | Young et al. |
| 2012/0001768 A1 | 1/2012 | Radosavljevic et al. |
| 2012/0004872 A1* | 1/2012 | Oh .......................... G01D 3/10 702/62 |
| 2012/0004886 A1 | 1/2012 | Jordil et al. |
| 2012/0007588 A1 | 1/2012 | Tan |
| 2012/0009918 A1 | 1/2012 | Wu |
| 2012/0022815 A1 | 1/2012 | Murakami et al. |
| 2012/0026005 A1 | 2/2012 | Myoung et al. |
| 2012/0029718 A1* | 2/2012 | Davis ..................... G05B 15/02 700/295 |
| 2012/0045988 A1 | 2/2012 | Blanton et al. |
| 2012/0046897 A1* | 2/2012 | Panko .................... G01R 15/12 702/67 |
| 2012/0047424 A1 | 2/2012 | Rothschild |
| 2012/0051242 A1 | 3/2012 | Rigomier et al. |
| 2012/0056755 A1* | 3/2012 | Hanft ..................... H04Q 9/00 340/870.07 |
| 2012/0062390 A1* | 3/2012 | Solomon ................ H04Q 9/00 340/870.03 |
| 2012/0083682 A1* | 4/2012 | Klodell ................. A61B 7/005 600/407 |
| 2012/0102078 A1 | 4/2012 | Flick et al. |
| 2012/0112701 A1* | 5/2012 | Ito ........................... H04Q 9/00 320/134 |
| 2012/0119791 A1 | 5/2012 | Hsiao |
| 2012/0122480 A1* | 5/2012 | Scalisi .................... G01S 19/19 455/456.1 |
| 2012/0130223 A1 | 5/2012 | Reicher |
| 2012/0138388 A1 | 6/2012 | Finschi et al. |
| 2012/0139952 A1* | 6/2012 | Imai ....................... G06F 3/1454 345/672 |
| 2012/0143387 A1 | 6/2012 | Indovina et al. |
| 2012/0146788 A1* | 6/2012 | Wilson ............... G08B 13/2491 340/539.23 |
| 2012/0154172 A1 | 6/2012 | O'Hara et al. |
| 2012/0154404 A1 | 6/2012 | Clement et al. |
| 2012/0157009 A1 | 6/2012 | Hollander et al. |
| 2012/0166233 A1* | 6/2012 | Wengrovitz .............. H04Q 9/00 705/7.11 |
| 2012/0172023 A1* | 7/2012 | Griff ....................... H04L 43/00 455/418 |
| 2012/0173032 A1 | 7/2012 | Pamulaparthy et al. |
| 2012/0178438 A1* | 7/2012 | Vashi ................... H04W 24/10 455/424 |
| 2012/0181974 A1 | 7/2012 | Kuniyosi et al. |
| 2012/0187883 A1 | 7/2012 | Valdez et al. |
| 2012/0224067 A1* | 9/2012 | Stuart ..................... G06F 16/58 348/164 |
| 2012/0229270 A1 | 9/2012 | Morley et al. |
| 2012/0245751 A1 | 9/2012 | Gow et al. |
| 2012/0245878 A1* | 9/2012 | Kane ...................... G05B 15/02 702/116 |
| 2012/0265586 A1* | 10/2012 | Mammone ............. G06Q 30/02 705/14.1 |
| 2012/0270505 A1 | 10/2012 | Prakash et al. |
| 2012/0271557 A1* | 10/2012 | Sekimoto .............. A61B 5/4866 702/19 |
| 2012/0275651 A1* | 11/2012 | Brown .................. G06T 11/206 382/103 |
| 2012/0278014 A1 | 11/2012 | Davies |
| 2012/0293337 A1 | 11/2012 | Carlsson |
| 2012/0296799 A1* | 11/2012 | Playfair ................. G06Q 30/00 705/37 |
| 2012/0296899 A1* | 11/2012 | Adams ................... G16H 10/40 707/736 |
| 2012/0300089 A1* | 11/2012 | Sbaiz .................. G06K 9/00671 348/222.1 |
| 2012/0306882 A1 | 12/2012 | Kashiwagi et al. |
| 2012/0310558 A1 | 12/2012 | Taft |
| 2012/0320189 A1* | 12/2012 | Stuart ..................... G01J 5/025 348/135 |
| 2012/0330615 A1* | 12/2012 | Cornwall ................ H04Q 9/00 702/185 |
| 2013/0009788 A1* | 1/2013 | Langenberg ........... G01D 4/002 340/870.02 |
| 2013/0023295 A1* | 1/2013 | Kasslin ................. H04W 48/14 455/501 |

(56) References Cited

U.S. PATENT DOCUMENTS

| | | | |
|---|---|---|---|
| 2013/0024149 A1* | 1/2013 | Nayar | G01R 29/18 702/72 |
| 2013/0027219 A1* | 1/2013 | Myoung | H04Q 9/00 340/870.03 |
| 2013/0027220 A1* | 1/2013 | Marwah | H04Q 9/00 340/870.01 |
| 2013/0029683 A1* | 1/2013 | Kim | H04L 67/12 455/456.1 |
| 2013/0035871 A1 | 2/2013 | Mayou et al. | |
| 2013/0040664 A1 | 2/2013 | Zhang et al. | |
| 2013/0041852 A1 | 2/2013 | Ellis et al. | |
| 2013/0050246 A1 | 2/2013 | Barry et al. | |
| 2013/0051498 A1* | 2/2013 | Taft | G01R 19/2513 375/340 |
| 2013/0064178 A1* | 3/2013 | Cs | H04Q 9/00 370/328 |
| 2013/0065633 A1 | 3/2013 | Sridhara et al. | |
| 2013/0066576 A1* | 3/2013 | Cs | G01R 15/142 702/66 |
| 2013/0069627 A1* | 3/2013 | Cs | G01R 19/2513 324/76.77 |
| 2013/0083193 A1 | 4/2013 | Okuyama et al. | |
| 2013/0106616 A1* | 5/2013 | Gustafsson | H04Q 9/00 340/870.02 |
| 2013/0106906 A1 | 5/2013 | Roche et al. | |
| 2013/0124136 A1* | 5/2013 | Neeley | G06F 11/2294 702/122 |
| 2013/0127904 A1 | 5/2013 | Dove et al. | |
| 2013/0128022 A1* | 5/2013 | Bose | G06Q 10/0833 348/77 |
| 2013/0137940 A1* | 5/2013 | Schafer | A61B 10/0012 600/301 |
| 2013/0147464 A1 | 6/2013 | Tan | |
| 2013/0150744 A1 | 6/2013 | Brattain et al. | |
| 2013/0158911 A1* | 6/2013 | Young | G01R 21/006 702/62 |
| 2013/0162442 A1* | 6/2013 | Honda | G08C 17/02 340/870.02 |
| 2013/0176141 A1* | 7/2013 | LaFrance | G08C 17/02 340/870.02 |
| 2013/0181845 A1* | 7/2013 | Johnson | H04Q 9/00 340/870.02 |
| 2013/0197835 A1 | 8/2013 | Jonsson et al. | |
| 2013/0204439 A1 | 8/2013 | Scelzi | |
| 2013/0204448 A1 | 8/2013 | Lee et al. | |
| 2013/0204554 A1 | 8/2013 | Tuckey et al. | |
| 2013/0211214 A1 | 8/2013 | Olsen | |
| 2013/0211557 A1 | 8/2013 | O'Brien | |
| 2013/0211731 A1* | 8/2013 | Woltman | G16H 40/20 702/21 |
| 2013/0215154 A1 | 8/2013 | Ponomarev et al. | |
| 2013/0215903 A1 | 8/2013 | Kotlicki et al. | |
| 2013/0231790 A1 | 9/2013 | Shao | |
| 2013/0241743 A1* | 9/2013 | Loic | H04Q 9/00 340/870.02 |
| 2013/0241746 A1* | 9/2013 | McKinley | G01R 19/2513 340/870.02 |
| 2013/0245965 A1 | 9/2013 | Kane et al. | |
| 2013/0249917 A1 | 9/2013 | Fanning et al. | |
| 2013/0253882 A1* | 9/2013 | Park | G06F 15/00 702/152 |
| 2013/0261821 A1* | 10/2013 | Lu | H04L 12/2836 700/289 |
| 2013/0262197 A1* | 10/2013 | Kaulgud | H02J 3/001 705/14.1 |
| 2013/0268620 A1* | 10/2013 | Osminer | H04N 21/8549 709/217 |
| 2013/0271467 A1* | 10/2013 | Misumi | G06Q 50/06 345/440 |
| 2013/0291060 A1 | 10/2013 | Moore | |
| 2013/0297259 A1 | 11/2013 | Tsao et al. | |
| 2013/0300747 A1 | 11/2013 | Wong et al. | |
| 2013/0307992 A1 | 11/2013 | Erlandsson et al. | |
| 2013/0321425 A1 | 12/2013 | Greene et al. | |
| 2013/0338958 A1* | 12/2013 | Shanishchara | G01C 25/00 702/116 |
| 2013/0342359 A1* | 12/2013 | Miyaji | G01D 4/002 340/870.03 |
| 2013/0344888 A1* | 12/2013 | Dousse | H04W 4/029 455/456.1 |
| 2014/0018111 A1* | 1/2014 | Farley | H04W 4/023 455/456.6 |
| 2014/0028854 A1 | 1/2014 | Heinke et al. | |
| 2014/0035607 A1 | 2/2014 | Heydron et al. | |
| 2014/0039838 A1 | 2/2014 | Katz et al. | |
| 2014/0039842 A1 | 2/2014 | Yuen et al. | |
| 2014/0051941 A1 | 2/2014 | Messerschmidt | |
| 2014/0052503 A1 | 2/2014 | Zaloom | |
| 2014/0067325 A1* | 3/2014 | McKee | H04Q 9/00 702/183 |
| 2014/0071136 A1 | 3/2014 | Lang | |
| 2014/0074257 A1* | 3/2014 | Bhargava | H04L 12/282 700/47 |
| 2014/0078151 A1 | 3/2014 | Garr et al. | |
| 2014/0095577 A1* | 4/2014 | Root et al. | |
| 2014/0142724 A1 | 5/2014 | Park et al. | |
| 2014/0152667 A1 | 6/2014 | Li et al. | |
| 2014/0163746 A1 | 6/2014 | Drew et al. | |
| 2014/0163927 A1* | 6/2014 | Molettiere | A61B 5/1112 702/189 |
| 2014/0164611 A1* | 6/2014 | Molettiere | A61B 5/1118 709/224 |
| 2014/0172772 A1 | 6/2014 | Sanchez Loureda | |
| 2014/0180968 A1 | 6/2014 | Song et al. | |
| 2014/0184604 A1 | 7/2014 | Bak et al. | |
| 2014/0187254 A1 | 7/2014 | Wang et al. | |
| 2014/0191573 A1 | 7/2014 | Chen et al. | |
| 2014/0210845 A1* | 7/2014 | Zazueta-Hall | G06T 11/206 345/589 |
| 2014/0212978 A1 | 7/2014 | Sharpe, Jr. et al. | |
| 2014/0215073 A1 | 7/2014 | Dow et al. | |
| 2014/0218383 A1 | 8/2014 | Srivastava | |
| 2014/0232549 A1 | 8/2014 | Shin et al. | |
| 2014/0232553 A1* | 8/2014 | Venkatraman | G01S 5/0036 340/870.07 |
| 2014/0236371 A1* | 8/2014 | Ishihara | H02J 13/00016 700/286 |
| 2014/0259133 A1 | 9/2014 | Alonso Diaz et al. | |
| 2014/0266669 A1* | 9/2014 | Fadell | G05B 19/042 340/501 |
| 2014/0266765 A1 | 9/2014 | Neeley et al. | |
| 2014/0267294 A1 | 9/2014 | Ma et al. | |
| 2014/0267296 A1* | 9/2014 | Neeley | G01D 7/08 345/440 |
| 2014/0267765 A1 | 9/2014 | Stuart et al. | |
| 2014/0270546 A1 | 9/2014 | Neeley et al. | |
| 2014/0274114 A1* | 9/2014 | Rowitch | G01S 5/0252 455/456.1 |
| 2014/0277792 A1 | 9/2014 | Kaufman | |
| 2014/0277814 A1* | 9/2014 | Hall | H02J 13/00026 700/298 |
| 2014/0277827 A1 | 9/2014 | Chinnadurai et al. | |
| 2014/0278255 A1* | 9/2014 | Anderson | G01R 15/125 702/189 |
| 2014/0278259 A1 | 9/2014 | Neeley et al. | |
| 2014/0279443 A1* | 9/2014 | Neeley | G01D 1/00 702/188 |
| 2014/0282145 A1 | 9/2014 | Dewan | |
| 2014/0282241 A1 | 9/2014 | Epperson et al. | |
| 2014/0289250 A1* | 9/2014 | Nojima | G05B 19/4183 707/737 |
| 2014/0289251 A1* | 9/2014 | Nojima | G05B 19/4183 707/737 |
| 2014/0297229 A1 | 10/2014 | Izumo et al. | |
| 2014/0300486 A1* | 10/2014 | Hummel | H04Q 9/00 340/870.01 |
| 2014/0313205 A1 | 10/2014 | Huempel et al. | |
| 2014/0324388 A1* | 10/2014 | Kriss | G01M 99/005 702/182 |
| 2014/0336837 A1 | 11/2014 | Kiuchi et al. | |

(56) References Cited

U.S. PATENT DOCUMENTS

| | | | |
|---|---|---|---|
| 2014/0340236 A1* | 11/2014 | Rhoads | G06Q 50/06 340/870.02 |
| 2014/0375428 A1 | 12/2014 | Park | |
| 2014/0375472 A1* | 12/2014 | Sankey | G01D 4/002 340/870.02 |
| 2014/0376377 A1 | 12/2014 | Mikoda et al. | |
| 2015/0012147 A1* | 1/2015 | Haghighat-Kashani | G06Q 50/06 700/291 |
| 2015/0019280 A1* | 1/2015 | Mejegard | H04W 24/08 705/7.23 |
| 2015/0022181 A1* | 1/2015 | Anderson | G06F 9/5005 324/114 |
| 2015/0022529 A1 | 1/2015 | Johnston | |
| 2015/0025701 A1 | 1/2015 | Huomo | |
| 2015/0035833 A1 | 2/2015 | Hao et al. | |
| 2015/0035834 A1* | 2/2015 | Axness | G01D 7/08 345/440 |
| 2015/0039269 A1* | 2/2015 | Mejegard | H04W 4/80 702/182 |
| 2015/0050902 A1* | 2/2015 | Umeki | H04Q 9/00 455/127.5 |
| 2015/0054830 A1* | 2/2015 | Inuzuka | G06T 11/206 345/440 |
| 2015/0061859 A1* | 3/2015 | Matsuoka | G08B 25/008 340/501 |
| 2015/0077269 A1* | 3/2015 | Hua | G08C 17/02 340/870.16 |
| 2015/0085136 A1* | 3/2015 | Bernal | H04N 25/443 348/335 |
| 2015/0088442 A1 | 3/2015 | Farrar et al. | |
| 2015/0090585 A1* | 4/2015 | Nosti | C25D 21/12 204/229.8 |
| 2015/0094874 A1* | 4/2015 | Hall | H02J 13/00024 700/297 |
| 2015/0095414 A1 | 4/2015 | Turbin | |
| 2015/0112617 A1 | 4/2015 | Suen et al. | |
| 2015/0120222 A1* | 4/2015 | Roytelman | H02J 13/00002 702/60 |
| 2015/0123814 A1* | 5/2015 | Wada | H04Q 9/00 340/870.03 |
| 2015/0133167 A1* | 5/2015 | Edge | H04W 4/025 455/456.3 |
| 2015/0149119 A1 | 5/2015 | Fansler | |
| 2015/0149122 A1 | 5/2015 | Cipri | |
| 2015/0160284 A1 | 6/2015 | Cern | |
| 2015/0185251 A1 | 7/2015 | Heydron et al. | |
| 2015/0185718 A1 | 7/2015 | Tappan et al. | |
| 2015/0190099 A1 | 7/2015 | Aratani | |
| 2015/0228097 A1 | 8/2015 | Matange et al. | |
| 2015/0242783 A1 | 8/2015 | Sasaki | |
| 2015/0271575 A1* | 9/2015 | Asao | H02S 50/10 340/870.07 |
| 2015/0276816 A1 | 10/2015 | Yoshida et al. | |
| 2015/0276830 A1 | 10/2015 | Airaksinen et al. | |
| 2015/0308856 A1 | 10/2015 | Srinivasan et al. | |
| 2015/0309089 A1 | 10/2015 | Katsukura et al. | |
| 2015/0323611 A1 | 11/2015 | Kise et al. | |
| 2015/0324439 A1* | 11/2015 | Bhave | G06F 16/335 707/607 |
| 2015/0355036 A1* | 12/2015 | Giorgi | G01K 13/00 702/182 |
| 2016/0028475 A1 | 1/2016 | Zhang et al. | |
| 2016/0041002 A1* | 2/2016 | Alzate Perez | G01D 4/004 340/870.02 |
| 2016/0048740 A1 | 2/2016 | Winter | |
| 2016/0049790 A1* | 2/2016 | Wordsworth | H02J 7/34 700/297 |
| 2016/0078127 A1 | 3/2016 | Bhat et al. | |
| 2016/0080666 A1* | 3/2016 | Stuart | G01R 13/0281 348/135 |
| 2016/0080667 A1* | 3/2016 | Stuart | H04N 23/11 348/135 |
| 2016/0109491 A1 | 4/2016 | Kann | |
| 2016/0117070 A1* | 4/2016 | Rose | G01D 4/004 715/738 |
| 2016/0119592 A1* | 4/2016 | Stuart | H04N 7/185 348/82 |
| 2016/0124022 A1 | 5/2016 | Tadano | |
| 2016/0140870 A1 | 5/2016 | Connor | |
| 2016/0149717 A1* | 5/2016 | Wada | H04L 12/2827 455/414.1 |
| 2016/0149721 A1* | 5/2016 | Wakeyama | G08B 13/19682 455/414.1 |
| 2016/0169577 A1 | 6/2016 | Watanabe et al. | |
| 2016/0171728 A1 | 6/2016 | Klein | |
| 2016/0180578 A1 | 6/2016 | Vegesna | |
| 2016/0188185 A1 | 6/2016 | Bous | |
| 2016/0190981 A1 | 6/2016 | Hong et al. | |
| 2016/0212506 A1 | 7/2016 | Norwood et al. | |
| 2016/0231372 A1 | 8/2016 | Wootton et al. | |
| 2016/0232457 A1 | 8/2016 | Gray et al. | |
| 2016/0238639 A1 | 8/2016 | Tadano | |
| 2016/0249831 A1 | 9/2016 | Eastman et al. | |
| 2016/0291608 A1 | 10/2016 | Reider et al. | |
| 2016/0294019 A1* | 10/2016 | Yamauchi | H01M 10/48 |
| 2016/0320432 A1 | 11/2016 | Nagai | |
| 2016/0321224 A1 | 11/2016 | Duncker et al. | |
| 2016/0322078 A1* | 11/2016 | Bose | G01P 13/00 |
| 2016/0327294 A1 | 11/2016 | Svendsen | |
| 2016/0335377 A1 | 11/2016 | Yamashina et al. | |
| 2016/0349954 A1 | 12/2016 | Thompson et al. | |
| 2016/0359325 A1 | 12/2016 | Kawata et al. | |
| 2016/0360464 A1 | 12/2016 | Han et al. | |
| 2016/0363956 A1* | 12/2016 | Moore | G06F 11/1471 |
| 2016/0370001 A1 | 12/2016 | Sim | |
| 2016/0371412 A1* | 12/2016 | Marie | G06F 3/0482 |
| 2016/0371662 A1* | 12/2016 | Fine | G06Q 30/02 |
| 2017/0004358 A1 | 1/2017 | Bose et al. | |
| 2017/0005515 A1 | 1/2017 | Sanders et al. | |
| 2017/0006435 A1 | 1/2017 | Yamamoto | |
| 2017/0017214 A1 | 1/2017 | O'Keeffe | |
| 2017/0019248 A1 | 1/2017 | Mustafa et al. | |
| 2017/0019809 A1 | 1/2017 | Saikusa | |
| 2017/0026800 A1 | 1/2017 | Kim et al. | |
| 2017/0030951 A1 | 2/2017 | Shon | |
| 2017/0041960 A1 | 2/2017 | Quan et al. | |
| 2017/0045868 A1 | 2/2017 | Cavarec et al. | |
| 2017/0048482 A1 | 2/2017 | Drako et al. | |
| 2017/0108351 A1* | 4/2017 | Shimizu | G01D 4/002 |
| 2017/0108456 A1 | 4/2017 | Alizadeh et al. | |
| 2017/0108904 A1 | 4/2017 | Choi et al. | |
| 2017/0109653 A1* | 4/2017 | Agarwal | G06F 16/285 |
| 2017/0122774 A1 | 5/2017 | Quady | |
| 2017/0123397 A1 | 5/2017 | Billi et al. | |
| 2017/0124350 A1 | 5/2017 | Reihman et al. | |
| 2017/0126843 A1 | 5/2017 | Pantea et al. | |
| 2017/0146429 A1 | 5/2017 | Suzuki | |
| 2017/0150069 A1 | 5/2017 | Parrish et al. | |
| 2017/0150239 A1* | 5/2017 | Davis | G08C 17/02 |
| 2017/0154445 A1 | 6/2017 | Maruhashi | |
| 2017/0155279 A1 | 6/2017 | Eckhardt et al. | |
| 2017/0171359 A1* | 6/2017 | Ando | H04L 41/0233 |
| 2017/0177546 A1 | 6/2017 | Heinz et al. | |
| 2017/0189751 A1 | 7/2017 | Knickerbocker et al. | |
| 2017/0193788 A1 | 7/2017 | Kim et al. | |
| 2017/0200294 A1* | 7/2017 | Hirano | G09G 5/14 |
| 2017/0205451 A1 | 7/2017 | Moinuddin | |
| 2017/0212668 A1* | 7/2017 | Shah | G06F 3/0486 |
| 2017/0215191 A1 | 7/2017 | Martin | |
| 2017/0219379 A1* | 8/2017 | Rapadas | G01D 4/006 |
| 2017/0223433 A1 | 8/2017 | Busslinger | |
| 2017/0229863 A1* | 8/2017 | Hall | H02J 3/00 |
| 2017/0249648 A1* | 8/2017 | Garvey | G06F 11/3452 |
| 2017/0265053 A1 | 9/2017 | Diebold et al. | |
| 2017/0271877 A1 | 9/2017 | Stewart et al. | |
| 2017/0285591 A1 | 10/2017 | Menzel | |
| 2017/0307245 A1* | 10/2017 | Itaya | F24F 11/30 |
| 2017/0307665 A1 | 10/2017 | Shinozaki | |
| 2017/0309094 A1* | 10/2017 | Farahat | G05B 23/0283 |
| 2017/0336930 A1* | 11/2017 | Tappan | G08B 21/18 |
| 2017/0363666 A1* | 12/2017 | Alkuran | H02J 13/00017 |

(56) References Cited

U.S. PATENT DOCUMENTS

| | | | |
|---|---|---|---|
| 2018/0003573 A1* | 1/2018 | Giorgi | H04L 12/2816 |
| 2018/0011626 A1 | 1/2018 | Kelley et al. | |
| 2018/0031618 A1* | 2/2018 | Friedlander et al. | |
| 2018/0040317 A1 | 2/2018 | Mochizuki et al. | |
| 2018/0042174 A1* | 2/2018 | Li | G06Q 10/06 |
| 2018/0049039 A1* | 2/2018 | Chandrasekaran | H04W 16/18 |
| 2018/0060741 A1 | 3/2018 | Sakai | |
| 2018/0066945 A1 | 3/2018 | Meier et al. | |
| 2018/0074099 A1* | 3/2018 | Takata | H04Q 9/00 |
| 2018/0090932 A1 | 3/2018 | Main et al. | |
| 2018/0090933 A1 | 3/2018 | Main et al. | |
| 2018/0138704 A1* | 5/2018 | Hall | H02J 3/24 |
| 2018/0140241 A1 | 5/2018 | Hamalainen et al. | |
| 2018/0143237 A1* | 5/2018 | Beaudet | G01R 31/42 |
| 2018/0165385 A1 | 6/2018 | Cillis et al. | |
| 2018/0165554 A1* | 6/2018 | Zhang | G06F 18/2411 |
| 2018/0165842 A1 | 6/2018 | Kumar | |
| 2018/0165844 A1 | 6/2018 | Kirichenko et al. | |
| 2018/0174337 A1 | 6/2018 | Menard et al. | |
| 2018/0180648 A1* | 6/2018 | Carson | G01R 15/144 |
| 2018/0189989 A1* | 7/2018 | Douglas | G06F 3/0346 |
| 2018/0197135 A1 | 7/2018 | Moyer et al. | |
| 2018/0197188 A1 | 7/2018 | Halstead et al. | |
| 2018/0199250 A1 | 7/2018 | Vare et al. | |
| 2018/0209922 A1 | 7/2018 | Yamakawa et al. | |
| 2018/0225600 A1 | 8/2018 | Govindugari | |
| 2018/0228432 A1 | 8/2018 | Woo et al. | |
| 2018/0242058 A1* | 8/2018 | Hayakawa | H04Q 9/02 |
| 2018/0248352 A1* | 8/2018 | Herazo | H02H 3/063 |
| 2018/0248403 A1 | 8/2018 | Takashita et al. | |
| 2018/0254661 A1* | 9/2018 | Toizumi | H04Q 9/00 |
| 2018/0255372 A1* | 9/2018 | Toizumi | G06N 7/01 |
| 2018/0268581 A1 | 9/2018 | Demuth | |
| 2018/0278091 A1* | 9/2018 | Fukasawa | H02J 13/00017 |
| 2018/0294647 A1 | 10/2018 | Borean et al. | |
| 2018/0320915 A1 | 11/2018 | Nagasaka | |
| 2018/0320967 A1* | 11/2018 | Kaloudis | G06F 17/13 |
| 2018/0321836 A1 | 11/2018 | Tappan et al. | |
| 2018/0322255 A1 | 11/2018 | Connell, II et al. | |
| 2018/0343506 A1 | 11/2018 | Busslinger | |
| 2018/0349365 A1 | 12/2018 | McRaven et al. | |
| 2018/0349563 A1 | 12/2018 | Bastide et al. | |
| 2018/0364689 A1 | 12/2018 | O'Brien | |
| 2019/0041439 A1* | 2/2019 | Brown | G01D 3/08 |
| 2019/0054347 A1* | 2/2019 | Saigh | G06F 18/00 |
| 2019/0082241 A1 | 3/2019 | Schmidt et al. | |
| 2019/0087990 A1 | 3/2019 | Hournbuckle, Jr. et al. | |
| 2019/0098377 A1* | 3/2019 | Kallus | H04B 3/54 |
| 2019/0162762 A1* | 5/2019 | Beck | G01R 21/133 |
| 2019/0213100 A1 | 7/2019 | Tayeb et al. | |
| 2019/0214954 A1* | 7/2019 | Coover | H04R 3/00 |
| 2019/0254629 A1* | 8/2019 | Li | A61B 8/08 |
| 2019/0271566 A1* | 9/2019 | Childers | H04Q 9/00 |
| 2019/0277898 A1* | 9/2019 | Beaudet | H04Q 9/02 |
| 2019/0279498 A1* | 9/2019 | Honda | G08C 17/00 |
| 2019/0281371 A1* | 9/2019 | Klicpera | H04Q 9/00 |
| 2019/0292013 A1* | 9/2019 | Ginsberg | G06F 16/447 |
| 2019/0293698 A1* | 9/2019 | Ventola | H02J 3/388 |
| 2019/0310167 A1* | 10/2019 | Kriss | G01N 29/00 |
| 2019/0325642 A1* | 10/2019 | Martinet | G06F 16/9024 |
| 2019/0342639 A1* | 11/2019 | Christiansen | H04L 1/0009 |
| 2019/0372345 A1* | 12/2019 | Bain | G06Q 30/0601 |
| 2019/0380046 A1* | 12/2019 | Johnson | H04B 17/318 |
| 2020/0007962 A1* | 1/2020 | Kuesel | H01Q 1/2208 |
| 2020/0008214 A1* | 1/2020 | Jeong | H04W 72/542 |
| 2020/0036635 A1* | 1/2020 | Ohuchi | H04L 43/0894 |
| 2020/0191607 A1* | 6/2020 | Sosna | G01D 4/004 |
| 2020/0309828 A1* | 10/2020 | Ahn | G01R 22/063 |
| 2020/0367821 A1* | 11/2020 | Redshaw | A61B 5/4875 |
| 2020/0374605 A1* | 11/2020 | Snook | H04Q 9/00 |
| 2021/0011071 A1* | 1/2021 | Adachi | H04Q 9/00 |
| 2021/0080514 A1* | 3/2021 | Beaudet | G01R 19/2513 |
| 2021/0088390 A1* | 3/2021 | Kriss | F24F 11/63 |
| 2021/0116517 A1* | 4/2021 | Snook, II | G01R 21/1331 |
| 2021/0117961 A1* | 4/2021 | Deshmukh | H04W 4/24 |
| 2021/0135890 A1* | 5/2021 | Arduini | H02J 13/00032 |
| 2021/0176541 A1* | 6/2021 | Okada | G08B 23/00 |
| 2021/0288520 A1* | 9/2021 | Cardozo | H04L 41/0816 |
| 2021/0329451 A1* | 10/2021 | Jun | H04L 63/0853 |
| 2022/0038930 A1* | 2/2022 | Fujisaki | H04J 3/06 |
| 2022/0101456 A1* | 3/2022 | Schönfeld | F17D 5/06 |
| 2022/0128388 A1* | 4/2022 | Raduchel | G01F 1/696 |
| 2022/0137600 A1* | 5/2022 | Ramos Peñuela | G05B 19/4183 |
| | | | 700/286 |
| 2022/0173767 A1* | 6/2022 | Barois | G08C 19/00 |
| 2022/0205890 A1* | 6/2022 | Chen | G01D 7/00 |
| 2022/0252485 A1* | 8/2022 | Strudwicke | G01D 21/00 |

FOREIGN PATENT DOCUMENTS

| | | |
|---|---|---|
| CN | 1443404 A | 9/2003 |
| CN | 101061523 A | 10/2007 |
| CN | 101326479 A | 12/2008 |
| CN | 101498744 A | 8/2009 |
| CN | 101782600 A | 7/2010 |
| CN | 102188263 A | 9/2011 |
| CN | 102568170 A | 7/2012 |
| CN | 202351298 U | 7/2012 |
| EP | 1 560 121 A1 | 8/2005 |
| EP | 1710593 A1 | 10/2006 |
| EP | 2 026 080 A2 | 2/2009 |
| EP | 2 254 253 A2 | 11/2010 |
| EP | 2 889 630 A1 | 7/2015 |
| JP | 2-294204 A | 12/1990 |
| JP | 8-68668 A | 3/1996 |
| JP | 2003-110749 A | 4/2003 |
| JP | 2003-302260 A | 10/2003 |
| JP | 2004-69641 A | 3/2004 |
| JP | 2010-9477 A | 1/2010 |
| JP | 2010-272118 A | 12/2010 |
| JP | 2011-258109 A | 12/2011 |
| KR | 10-2008-0112692 A | 12/2008 |
| KR | 10-2012-0065540 A | 6/2012 |
| KR | 10-2012-0077332 A | 7/2012 |
| WO | 2013/020110 A2 | 2/2013 |

OTHER PUBLICATIONS

Extech Instruments, "Extech EX540 Wireless Datalogging selected as 2010 EC&M Product of the Year Category Winner," Press Release, Mar. 18, 2009, 2 pages.

Extech Instruments, "Extech EX845 METERLiNK™ Clamp Meter Transmit Readings to FLIR IR Cameras," Press Release, Apr. 1, 2010, 3 pages.

Extech Instruments, "MultiMeter/Datalogger with Wireless PC Interface," Product Datasheet, Jul. 14, 2011, 1 page.

Extech Instruments, "Wireless TRMS Multimeter—Model EX540," User's Guide, Apr. 1, 2010, 17 pages.

Extended European Search Report, dated Jun. 1, 2015, for European Application No. 14200521.4-1560, 9 pages.

Extended European Search Report, dated Nov. 11, 2013, for European Application No. 13178568.5-1560, 8 pages.

Extended European Search Report, dated Oct. 20, 2016, for European Application No. 14762404.3-1568 / 2973108, 7 pages.

Extended European Search Report, dated Sep. 10, 2013, for European Application No. 13178211.2-1853, 8 pages.

"Fluke 3000 FC Fluke Connect Series Wireless Digital Multimeter," retrieved from http://www.testequity.com/products/5220, retrieved on Sep. 1, 2015, 2 pages.

Fluke, "1652C/1653B/1654B Electrical Installation Tester," User's Manual, Sep. 2010, 66 pages.

Fluke, "Basic electrical installation testing," Application Note, 2014, 4 pages.

Fluke, "Performing Live-Circuit Installation Tests with a Fluke 1650 series Tester on an IT-system," Application Note, 2004, 8 pages.

Fluke, "Testing RCDs with the Fluke 1650B Series," Application Note, 2014, 2 pages.

Fluke, "The importance of loop impedance testing," Application Note, 2003, 2 pages.

(56) References Cited

OTHER PUBLICATIONS

Hoh et al., Wireless Remote Connectivity with Handheld Digital Multimeters, 2012, retrieved from, http://www.wirelessdesignmag.com/blog/2012/03/wireless-remote-connectivity-handheld-digital-multimeters, retrieved on Sep. 1, 2015, 6 pages.

International Search Report dated Jul. 10, 2014, for International Application No. PCT/US2014/029561, 3 pages.

International Search Report and Written Opinion dated Sep. 12, 2014, for International Application No. PCT/US2014/029867, 12 pages.

International Search Report and Written Opinion dated Jul. 17, 2014, for International Application No. PCT/US2014/029889, 11 pages.

International Search Report and Written Opinion dated Jul. 18, 2014, for International Application No. PCT/US2014/029885, 13 pages.

International Search Report and Written Opinion dated Jul. 22, 2014, for International Application No. PCT/US2014/029883, 11 pages.

International Search Report and Written Opinion dated Jul. 24, 2014, for International Application No. PCT/US2014/029879, 10 pages.

Japanese Office Action, dated Jan. 23, 2018, for Japanese Application No. 2016-503271, 10 pages (with English translation).

Office Action for JP Application No. 2016-503271 dated Dec. 4, 2018, 8 pages.

Office Action, for Chinese Application No. 201480027748.9, dated Nov. 2, 2016, 22 pages. (with English Translation).

Office Action, dated Oct. 31, 2016, for Chinese Application No. 201310334993.1, 30 pages. (with English Translation).

Redfish Instruments, "iDVM v1.0 User's Guide," 2013, 21 pages.

Redfish Instruments, "iDVM," Screenshot, retrieved from http://appshopper.com/utilities/idvm, retrieved 2013, 2 pages.

* cited by examiner

AUTOMATED COMBINED DISPLAY OF MEASUREMENT DATA

CROSS-REFERENCE TO RELATED APPLICATIONS

This application is a continuation of U.S. application Ser. No. 14/214,662, filed Mar. 15, 2014, which claims the benefit of U.S. Provisional Application No. 61/801,380, filed Mar. 15, 2013, and U.S. Provisional Application No. 61/876,719, filed Sep. 11, 2013, the disclosures of which are incorporated by reference herein in their entirety.

BACKGROUND

Measurement tools such as digital multimeter (DMM) devices, heat-sensing infrared cameras, vibration meters, and the like are used in a wide array of industrial, commercial, and residential settings to measure a variety of properties of equipment. In production facilities, plants, and factories, for example, it is critical to ensure that equipment remains operational. Interruptions in production for unexpected failure of equipment can be costly. Such facilities typically establish procedures for routine monitoring and maintenance of equipment that include using measurement tools.

For example, a technician using a handheld measurement tool may be tasked to periodically measure a property of equipment to assess the functional "health" of the equipment or to determine the presence of a fault. To perform such measurements, the technician travels to the site of the equipment, manually records data from the measurement tool, and returns to a central location to produce a report. Unfortunately, the technician may need to return multiple times to the site of the equipment to obtain the desired data. Further, analysis of measured data obtained from the equipment often requires the technician to manually enter the measured data into a computer.

In some instances, an equipment maintenance process includes obtaining readings of measurement data from multiple measurement tools at different locations, and sometimes includes obtaining measurements simultaneously or in close time proximity. Furthermore, complex calculations may be desired to be quickly performed on measured data obtained at the different locations, even when using measurement tools with limited or no functionality for storing or processing measurements over time. What is desired are systems and methods that allow guidance and coordination to be provided with respect to collecting measurements using measurement tools, and that allow measurement data to be efficiently collected and processed.

SUMMARY

The following summary is provided to introduce a selection of concepts in a simplified form that are further described below in the Detailed Description. This summary is not intended to identify key features of the claimed subject matter, nor is it intended to be used as an aid in determining the scope of the claimed subject matter.

In some embodiments, a computer-implemented method for automatically generating a combined display of measurement data is provided. A mobile computing device establishes communication connections with a plurality of measurement devices configured to generate measurement data. The mobile computing device receives measurement data generated by the plurality of measurement devices and, in response to information indicative of the measurement data representing related parts of a combined measurement, the mobile computing device automatically groups the measurement data received from the plurality of measurement devices and automatically displays the grouped measurement data in a combined display of the measurement data that shares at least one axis of measurement. For example, the combined measurement may be a multiphase parameter in which the related parts are the individual phases of the parameter. The measurement data received from each measurement device may represent a phase of the multiphase parameter.

According to further aspects, the multiphase parameter may be an electrical parameter having at least three component phases. The combined display may include three component phases of a three-phase voltage, current, or power parameter, and wherein the at least one axis of measurement represents time.

According to further aspects, the information indicative of the measurement data representing related parts of a combined measurement may include time information indicating a proximity of time when the measurement data was generated by the plurality of measurement devices. The time information may indicate that the measurement data was generated by the measurement devices during an overlapping time interval.

According to further aspects, the information indicative of the measurement data representing related parts of a combined measurement may include location information indicating a proximity of location where the measurement data was generated by the plurality of measurement devices. The location information may indicate that the measurement data was generated by the measurement devices at an equipment test point.

According to further aspects, the combined display of the measurement data may share at least two axes of measurement. The combined display may be a graph of the measurement data, and the measurement data received from the plurality of measurement devices may be superimposed in the graph using the at least two axes of measurement.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

In various embodiments, disclosed herein are systems and methods for capturing, storing, analyzing, and reporting data obtained from measurement devices, such as handheld measurement tools and other sensors that perform measurements of equipment. Such systems and methods are useful, in part, for improving the speed, accuracy, and ease of use of measurement data collected from measurement devices, especially where the measurement data results from multiple simultaneous or near simultaneous measurements of different types of data.

As will be better understood from the following description, the term "measurement data" refers to data that is generated by a measurement device and directly or indirectly relates to or reflects a measured property of a device under test. In various embodiments, measurement devices may measure many types of properties, such as electrical and/or mechanical properties. Properties that may be measured by measurement devices include, for example and without limitation, electrical current, voltage, resistance, capacitance, inductance, vibration, humidity, pressure, light, time, temperature, sound, material composition, and the like.

Figure 1:
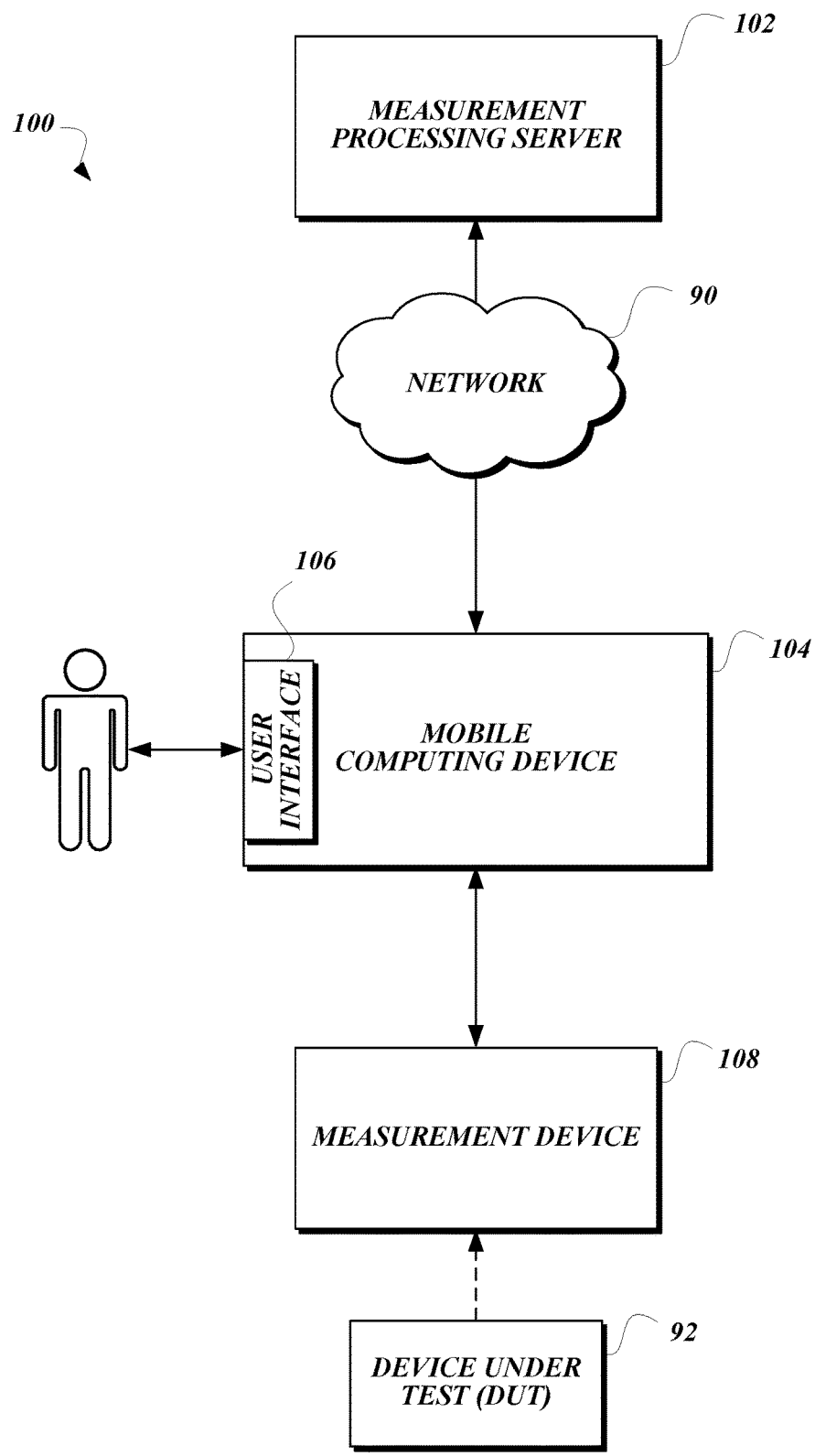
FIG. 1 is a schematic diagram that illustrates, at a high level, an exemplary embodiment of a system according to various aspects of the present disclosure.

FIG. 1 is a schematic diagram that illustrates, at a high level, an exemplary embodiment of a system according to various aspects of the present disclosure. In the illustrated embodiment, the system 100 includes a mobile computing device 104. The mobile computing device 104 is configured to interact with at least one measurement device 108 positioned with respect to equipment to be measured, such as the illustrated device under test (DUT) 92.

In some embodiments, the mobile computing device 104 may be a general purpose mobile computing device, such as a smart phone that provides cellular telephony, cellular data, Bluetooth, Wi-Fi, and/or other types of wireless connectivity, which is further programmed to provide functions as described herein. An application (or "app") executing on the mobile computing device 104 may provide processes for data collection, storage, analysis, and communication as described herein. A user interface 106 is presented by the mobile computing device 104, which allows a user to view data that is collected and analyzed by the computing device 104, and to control the collection, processing, storage, and transmission thereof as discussed further below.

In various embodiments, the measurement device 108 may be, for example, a measurement tool such as a DMM, a Wi-Fi network tester, a vibration tester, an infrared or thermal imaging camera, and/or the like that is capable of measuring a property of a DUT 92 and providing measurement data based thereon. Generally, measurement devices 108 may be handheld or portable, and may include any type of testing or sensing device or multipurpose device capable of performing a measurement or a combination of types of measurements. Measurement devices 108 may also include single purpose or multi-purpose sensors that are capable of measuring properties of equipment.

In various embodiments, data communication between measurement devices 108 and the mobile computing device 104 may be wireless or wired, and may use any type of standardized or proprietary communication protocol. Current standardized protocols for wired communication include, for example, USB, Firewire, Ethernet, and the like, while wireless data communication may be performed using ZigBee, Bluetooth, Wi-Fi, cellular data transmission protocols, and the like. The communication may be a direct communication between the measurement device 108 and the mobile computing device 104, or may take place over a network with one or more intervening network devices providing a communication path. In some embodiments, at least some of the processing described herein as being performed by the mobile computing device 104 could be performed by the measurement processing server 102. In such embodiments, the measurement device 108 may be configurable to communicate directly with the measurement processing server 102 via a wireless or wired communication path, and may use any type of standardized or proprietary communication protocol, including but not limited to the illustrated network 90.

In an environment where multiple measurement devices 108 are used to measure different properties of equipment, the mobile computing device 104 may be configured to choose measurement devices 108 with which to communicatively interact to receive measurement data, as well as analyze, display, and further communicate the measurement data to one or more locations remote from the equipment and/or the mobile computing device 104.

In at least one implementation, a user may establish communication links between the mobile computing device 104 and one or more measurement devices 108 that are positioned with respect to one or more DUTs 92. As each communication link is established, measurement data generated by the respective measurement devices 108 may automatically be communicated to the mobile computing device 104. When measurement data is no longer received from a measurement device 108, e.g., the measurement device 108 drops out of range of the mobile computing device 104, the mobile computing device 104 discontinues or releases the communication link. As will be discussed in greater detail below, measurement data previously received from the measurement device 108 may be stored by the mobile computing device 104 in association with the measurement device 108 and/or the test point (or points) being measured on the equipment, but upon discontinuing or releasing the communication link, the mobile computing device 104 no longer displays live data measurements from the measurement device 108 nor indicates an active communication link with the measurement device 108.

When the user no longer desires to receive measurement data from a particular measurement device 108, the user may cause the mobile computing device 104 to disconnect or release the communication link with the measurement device 108. Subsequently, the measurement device 108 may return to a low power operational mode in which the measurement device 108 periodically communicates a presence detect signal, as previously described. If desired, the measurement device 108 may be configured to locally store measurement data in a data store present on the measurement device 108, which later may be read by a mobile computing device 104 upon establishing a new communication link with the measurement device 108.

In some wireless environments, the mobile computing device 104 may be paired with a measurement device 108 in order to receive measurement data from the measurement device 108. Pairing adds a layer of security over such communication between the measurement device 108 and the mobile computing device 104 in that establishing a communication link with the measurement device 108 may utilize additional data that is typically accessible only to persons or devices authorized to engage in such communication.

As measurement data is received, the mobile computing device 104 may display the measurement data to the user via the user interface 106. In some embodiments, the displayed measurement data represents instantaneous measurements received from the measurement devices 108. When storage of the measurement data is desired, the user may initiate collection of the measurement data, such as by pressing a "Capture" or "Record" button on the user interface 106. For example, in at least one implementation, pressing a "Capture" button on the user interface 106 may cause the mobile computing device 104 to save a single set of the measurement data obtained at an instance of time. On the other hand, by pressing a "Record" button, the user may initiate a recording of multiple sets of the measurement data in which the mobile computing device 104 saves a time series of the measurement data received from the measurement device 108. If desired, such recordings may be presented to the user as a data graph or an image video on the display of the mobile computing device 104.

In some embodiments, the data obtained by the mobile computing device 104 may further include status or safety information regarding the measurement device 108 (as opposed to the DUT 92). For instance, if the status of the measurement device 108 justifies display of a warning light on the measurement device 108, information regarding that status may be transmitted to the mobile computing device 104 and a corresponding icon may be displayed on the mobile computing device 104 noting the condition of the measurement device 108. Some nonlimiting examples of a status that would justify the display of a warning light include a low battery status, an out-of-range indicator, a lead indicator, and the like. This may be particularly helpful to a user whose mobile computing device 104 is connected to multiple measurement devices 108. Such icon display helps the user to recognize when one or more of the measurement devices 108 need attention to ensure that correct measurement data is being obtained.

In some embodiments, data may also be conveyed between a measurement device 108 and the mobile computing device 104 using techniques other than via a communication protocol as described above. As a nonlimiting example, in some embodiments, data may be exchanged between the measurement device 108 and the mobile computing device 104 through transfer of physical media, such as a memory card that is transferred between memory slots in the measurement device 108 and the mobile computing device 104. As another nonlimiting example, in some embodiments, data may be displayed by the measurement device 108 in a human-readable format (such as via an analog instrument meter with analog display, or via a LCD or other indicator that presents a digital value) and the mobile computing device 104 may obtain the measurement data by capturing and processing an image of the measurement device 108. In yet another nonlimiting example, in some embodiments, data may be displayed by the measurement device 108, and a user may manually enter the data into the mobile computing device 104 via the user interface 106.

While in some embodiments, the mobile computing device 104 is the device in the system 100 responsible for obtaining, processing, and storing measurement data from measurement devices 108, in other embodiments, the mobile computing device 104 may also or instead communicate the measurement data to one or more measurement processing servers 102, which may be located at one or more local or remote locations. Such communication may be performed through a network 90 such as a wired or wireless network, and may involve local, wide area, or global data communication links, such as the Internet. In some embodiments, such communication may be performed by syncing the mobile computing device 104 to another computing device (such as a desktop computing device, a laptop computing device, a tablet computing device, and/or the like) via a dock, a physical communication cable, a wireless communication technology, or a network, and the other computing device may then act as the measurement processing server 102. In some embodiments, the other computing device may receive the data from the mobile computing device 104 and then subsequently transmit the data to the measurement processing server 102 via the network 90. In some embodiments, the mobile computing device 104 may obtain, process, and store the measurement data locally while unable to access the network 90, such as when there is no access to a cellular data network due to a lack of wireless signal strength at a measurement location. The mobile computing device 104 may then transmit the measurement data to one or more measurement processing servers 102 as discussed above upon being reconnected to a network 90 or otherwise communicatively coupled to another computing device.

Figure 2:
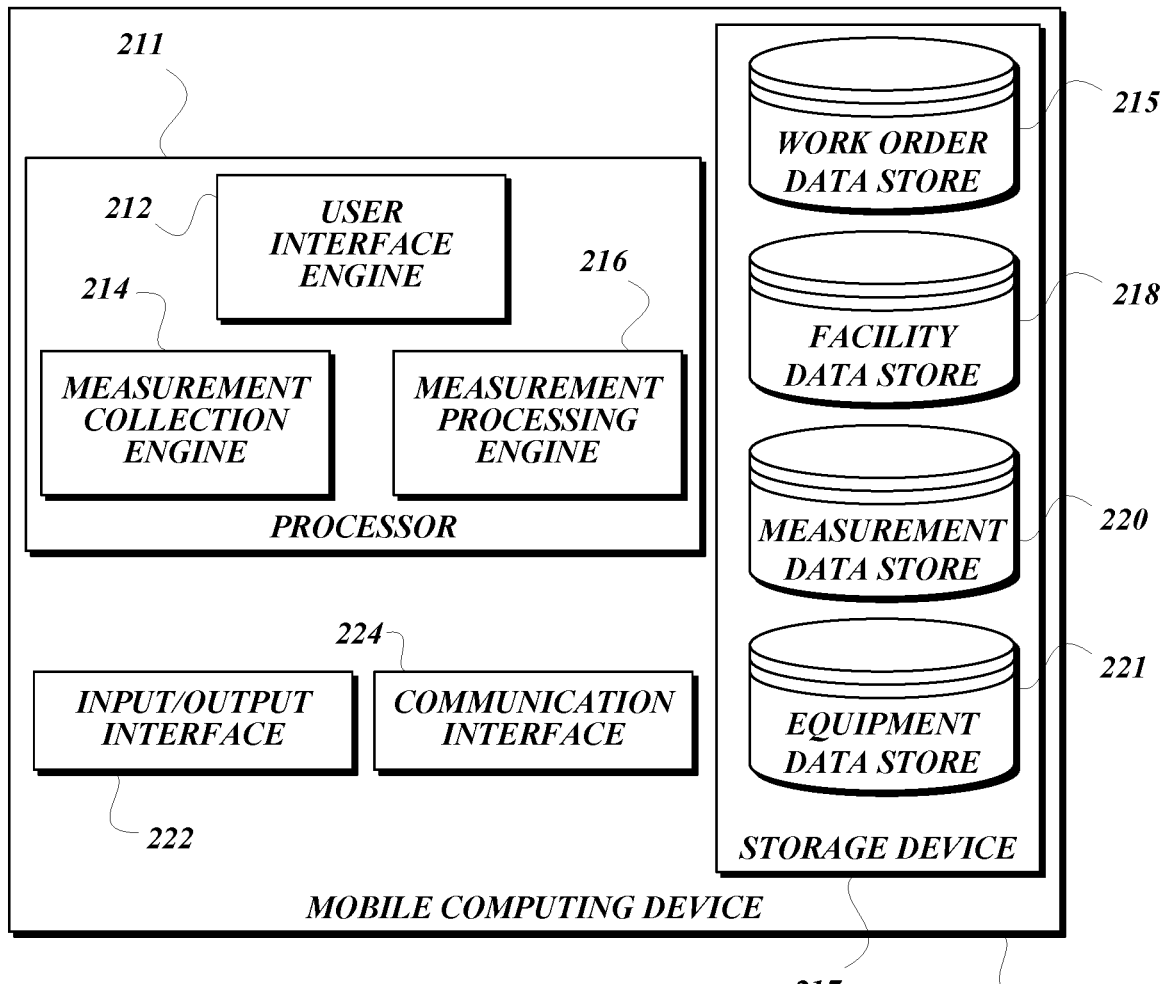
FIG. 2 is a block diagram that illustrates an exemplary mobile computing device according to various aspects of the present disclosure.

FIG. 2 is a block diagram that illustrates an exemplary mobile computing device 104 according to various aspects of the present disclosure. As illustrated, the mobile computing device 104 may include a processor 211, at least one communication interface 224, at least one data storage device 217, and at least one input/output (I/O) interface 222, among other elements. As used herein, the term processor is not limited to integrated circuitry otherwise referred to as a computer, but broadly refers to a microcontroller, a microcomputer, a microprocessor, a programmable logic controller, an application specific integrated circuit, other programmable circuits, combinations of the above, and/or the like. The processor 211 generally serves as a computational center of the mobile computing device 104 by supporting the execution of instructions that cause the device to receive, store, analyze, and communicate data using the communication interface 224, the storage device 217, and/or the input/output interface 222.

The communication interface 224 may include one or more components configured to communicate with external devices, such as another mobile computing device, a computer system at a remote location, a measurement device 108, and/or the like. All such communication may be wired or wireless. In some embodiments, the mobile computing device 104 may process measurement data into different forms and communicate the processed measurement data to such external devices. In some embodiments, the measurement data is organized and stored by the mobile computing device 104 in the storage device 217. The stored measurement data may later be retrieved, analyzed, and communicated.

The storage device 217 may comprise any form of computer-readable storage media, such as any currently available or later developed media suitable for storing computer-executable instructions and data that are accessible to one or more device components, such as the processor 211. Computer-readable storage media may be removable or nonremovable and may be volatile or nonvolatile. Examples of computer-readable storage media may include hard drives as well as RAM, ROM, EEPROM, flash types of memory, and/or the like.

The input/output interface 222 may include one or more input devices such as dials, switches, or buttons, and one or more output devices, such as a display or printer. Generally, the input/output interface 222 allows a user or an external system to interact with programs being executed by the mobile computing device 104. In at least one embodiment, the input/output interface 222 allows a user to control or configure the mobile computing device 104 to receive data from a measurement device 108 and to analyze, store, and/or communicate the measurement data to an external device. Information regarding the configuration of measurement devices and the equipment properties that they measure may be stored in the storage device 217 and used by the processor 212 when interacting with the measurement devices 108.

As an output device, a display may include, without limitation, a liquid crystal display (LCD), a light emitting diode (LED) device, an organic light emitting diode (OLED) device, and/or the like. The display may be capable of displaying color images, though embodiments disclosed herein also work with black and white displays. The display may include a touch screen that, in some embodiments, incorporates aspects of an input device into the display. The touch screen may be any type of touch screen currently known or later developed. For example, the touch screen may be a capacitive, infrared, resistive, or surface acoustic wave (SAW) device. In response to input received by the input device, the mobile computing device 104 may receive, analyze, store, and communicate data related to measurement of properties of equipment. In some measurement applications, the touch screen may be suitable for use in industrial settings, for example, where the touch screen is configured to receive inputs through gloved hands.

In addition to a touch screen or other display, the input/output interface 222 of the mobile computing device 104 may further include one or more input devices that communicate an input to the mobile computing device 104. As mentioned earlier, such input device may include, as examples, buttons, switches, trigger switches, selectors, rotary switches, or other input devices known to those of ordinary skill in the art. In at least one embodiment, measurement devices may be configured to perform measurements in response to user input or user selection of an input that is provided to the mobile computing device 104 via the one or more input devices.

As illustrated, the processor 211 may be configured to provide one or more engines. In general, the term "engine," as used herein, refers to logic embodied in hardware or software instructions, which can be written in a programming language, such as C, C++, COBOL, JAVA™, PHP, Perl, HTML, CSS, JavaScript, VBScript, ASPX, Objective C, Ruby, Microsoft .NET™ languages such as C #, and/or the like. An engine may be compiled into executable programs or written in interpreted programming languages. Software engines or applications may be callable from other engines or from themselves. Generally, the engines described herein refer to logical modules that can be merged with other engines or applications, or can be divided into sub-engines. The engines can be stored in any type of computer-readable medium or computer storage device, such as the storage device 217, and be stored on and executed by one or more general purpose processors (such as processor 211), thus creating a special purpose computing device configured to provide the engine. In some embodiments, the engines described herein may be incorporated into one or more applications or "apps" installed on the mobile computing device 104. The illustrated engines may be provided by the processor 211 in response to execution by the processor of computer-executable instructions stored on a computer-readable medium, such as the storage device 217.

As illustrated, the engines provided by the processor 211 may include a user interface engine 212, a measurement collection engine 214, and a measurement processing engine 216. The measurement collection engine 214 is configured to interact with one or more measurement devices 108 via the communication interface 224. The measurement collection engine 214 may instruct the measurement devices 108 to obtain measurement data, and may receive measurement data from the measurement devices 108. The measurement collection engine 214 may also store the received measurement data in the measurement data store 220. Additionally, the measurement collection engine 214 may receive warning status information from the measurement devices 108, and may cause the user interface engine 212 to present corresponding icons and/or notifications. The measurement processing engine 216 may perform processing over measurements stored in the measurement data store 220, or may process measurements obtained by the measurement collection engine 214 before storage in the measurement data store 220. For example, the measurement processing engine 216 may group measurements with other related measurements, may assign metadata to a received measurement, and/or perform other processing on the measurements as described elsewhere herein. As will be described below, the metadata includes group identifying information that associates the stored measurement data with other data annotated with similar group identifying information.

The user interface engine 212 is configured to generate a user interface for presentation to a user via the input/output interface 222 of the mobile computing device 104. The user interface generated by the user interface engine 212 may allow the user to configure the measurement collection engine 214 to communicate with various measurement devices 108, and may allow the user to configure the measurement devices 108 to capture measurements per the user's input. The user interface generated by the user interface engine 212 may allow the user to instruct the measurement collection engine 214 to store a given measurement or a time series of measurements, may allow the user to observe currently obtained measurements, and may allow the user to browse and/or compare previously collected and stored measurements.

In some embodiments, the interface provided by the user interface engine 212 may also provide guidance to the user for assisting in collecting measurements. For example, in some embodiments, the user interface engine 212 may be configured to present a task list to the user representing a set of measurements to be obtained. In some embodiments, the user interface engine 212 may be configured to present a map to the user in order to guide the user to a location at which measurements are to be obtained, to assist the user in identifying equipment from which measurements have been obtained, and/or to assist the user in locating test points to be monitored on the equipment.

As illustrated, the storage device 217 may include a work order data store 215, a facility data store 218, a measurement data store 220, and an equipment data store 221. The measurement data store 220 may be configured to store measurements received by the mobile computing device 104, and also may be configured to store metadata associated with said measurements. The facility data store 218 may be configured to store information about a facility, such as floor plans, equipment locations, identifiers of installed equipment, test points on the equipment, and/or the like. The equipment data store 221 may be configured to store information about equipment that has been monitored (or is intended to be monitored in the future) using the system 100. For example, in some embodiments the equipment data store 221 may store information associated with units of equipment such as location information, model information, make information, equipment identifiers, photos, and test points. The work order data store 215 may be configured to store work order information that helps guide a user through a series of measurements to be completed. In some embodiments, the work order data store 215 may also be configured to store progress information along with a given work order to indicate which tasks within the work order have been completed and which are yet to be performed.

As understood by one of ordinary skill in the art, a "data store" as described herein may be any suitable device, or a data structure on a computer-readable medium, configured to store data for access by a computing device. One example of a data store is data stored in an organized manner on a storage medium such as storage device 217. Another example of a data store (which may be more relevant to the data stores provided by the measurement processing server 102 described further below) is a highly reliable, high-speed relational database management system (DBMS) executing on one or more computing devices and accessible over a high-speed packet switched network. Yet another example of a data store is a non-relational network-based storage system, such as the Amazon S3 store provided by Amazon.com, Inc., Google Cloud Storage provided by Google, Inc., a distributed hash table (DHT), and/or the like. However, any other suitable storage technique and/or device capable of quickly and reliably providing the stored data in response to queries may be used to provide a data store, and the computing device may be accessible locally instead of over a network, or may be accessible over some other type of suitable network or provided as a cloud-based service. For example, though the data stores in FIG. 2 are illustrated as being present on the storage device 217 of the mobile computing device 104, in some embodiments, the data stores may not be resident on the mobile computing device 104 but may instead be remotely accessible by the mobile computing device 104. One of ordinary skill in the art will recognize that separate data stores described herein may be combined into a single data store, and/or a single data store described herein may be separated into multiple data stores, without departing from the scope of the present disclosure.

Figure 3:
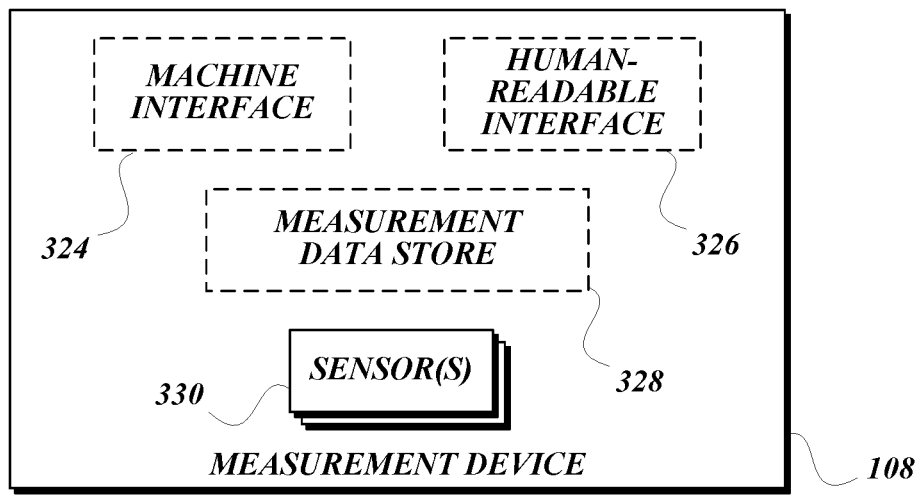
FIG. 3 is a block diagram that illustrates an exemplary embodiment of a measurement device according to various aspects of the present disclosure.

FIG. 3 is a block diagram that illustrates an exemplary embodiment of a measurement device according to various aspects of the present disclosure. As illustrated, the measurement device 108 includes one or more sensors 330, and optionally includes a machine interface 324, a human-readable interface 326, and a measurement data store 328.

The sensors 330 are devices associated with the measurement device 108 that collect information regarding properties of a device under test, and convert the information to a useable form. For example, a voltage sensor may sense a voltage across two test leads applied to the device under test, and may output a value indicating the sensed voltage for use by other components of the measurement device 108. Likewise, a temperature sensor may detect a temperature of a portion of the device under test, and may output a value indicating the temperature. In some embodiments, the sensors 330 may be integrated into a single case along with the rest of the components of the measurement device 108. In some embodiments, one or more of the sensors 330 may be located external from a case containing other components of the measurement device 108, and may communicate to the measurement device 108 using any suitable technique.

In some embodiments, the measurement device 108 may include one or more sensors 330 that are placed on or near test points of the equipment to be measured. Such sensors 330 may be temporarily affixed to the equipment or to structures near the equipment. Alternatively or in addition, the sensors 330 may be incorporated into test devices that a user can relocate from one test point to another on the equipment as needed.

In some embodiments, the measurement device 108 may be a handheld measurement tool. A handheld measurement tool is generally configured to be held in a user's hand while measuring a property of equipment. However, it should be appreciated that a handheld measurement tool need not always be held in a user's hand and may be positioned by a user away from the user's hand, for example, by affixing or hanging the tool from a support or placing the tool on or near a test point on the equipment to be measured. In some embodiments, the measurement device 108 is a device other than a handheld measurement tool. For example, the measurement device 108 may be, for example, a portable measurement tool that is not necessarily intended to be used while held in the hand. While not permanently connected to the equipment being measured, such portable tools are useful for measuring properties of the equipment over days or weeks, as desired.

In some instances, the measurement device 108 may log measurements of equipment properties over time, and may store the measurements in the measurement data store 328. Later, the mobile computing device 104 may obtain the measurements stored in the measurement data store 328. In some embodiments, the stored measurements may be obtained by the mobile computing device 104 via the machine interface 324, if the machine interface 324 is available, or via the human-readable interface 326, if the human-readable interface 326 is available and provides access to the stored measurements.

In some embodiments, the measurement data store 328 may be omitted. In such embodiments, the mobile computing device 104 may collect measurements from the sensors 330 via the machine interface 324 or the human-readable interface 326 as they are obtained by the sensors 330. The mobile computing device 104 may then provide storage functionality by storing the measurements in the measurement data store 220, thus allowing historical measurements to be collected, analyzed, and presented even when the measurement device 108 does not itself include a measurement data store 328. When desired, the mobile computing device 104 may display one or more graphs showing the measurement data as received over time, even from the measurement devices 108 that do not include the measurement data store 328.

The machine interface 324 may be any suitable machine-readable interface, such as a wireless communication interface or a wired communication interface as discussed above. In some embodiments, the machine interface 324 may be used to obtain measurements from the sensors 330 in real time or substantially in real time as measurements are obtained by the sensors 330, with or without the measurements being stored in the measurement data store 328. In some instances, the measurement device 108 may also include a human-readable interface 326. The human-readable interface 326 may display values obtained by the sensors 330 to the user in real time or substantially real time, and may provide access to stored past measurements in the measurement data store 328. The human-readable interface 326 may include a video display, a LCD display, an analog display, an indicator light, or any other suitable display. In some embodiments, similar information may be obtained via the machine interface 324 and the human-readable interface 326, while in some embodiments, different information may be obtained via the two interfaces.

Figure 4:
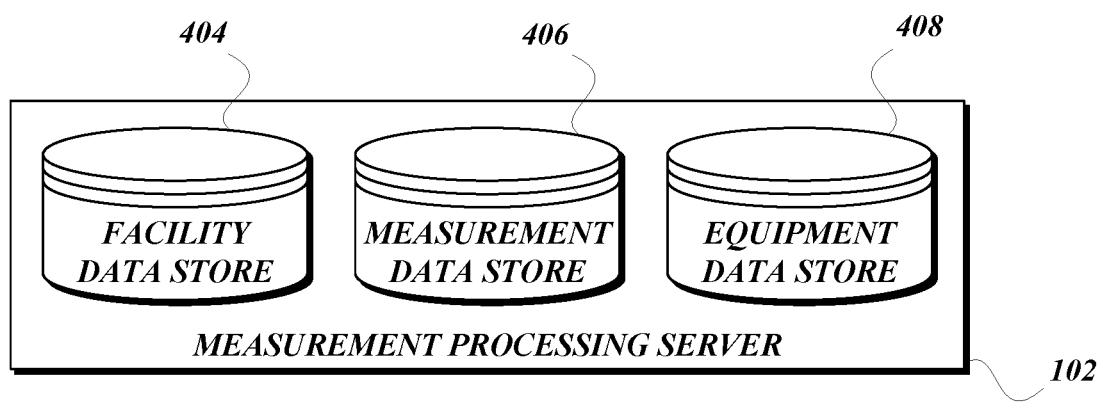
FIG. 4 is a block diagram that illustrates an exemplary embodiment of a measurement processing server according to various aspects of the present disclosure.

FIG. 4 is a block diagram that illustrates an exemplary embodiment of a measurement processing server 102 according to various aspects of the present disclosure. As illustrated, the measurement processing server 102 may be configured to provide a facility data store 404, a measurement data store 406, an equipment data store 408, and a work order data store 409. The facility data store 404, the measurement data store 406, and the work order data store 409 may be configured to store information similar to that stored by the facility data store 218, the measurement data store 220, and the work order data store 215, respectively, discussed above with respect to FIG. 2. However, in some embodiments, the data stores present on the measurement processing server 102 may receive and store data collected by more than one mobile computing device 104, or provided by multiple management computing devices for distribution to mobile computing devices 104. This may be useful for many purposes, including but not limited to comparing measurements taken of similar equipment at different locations and different times, centralized distribution of task lists and equipment information, and the like.

The equipment data store 408 may be configured to store information about equipment of particular makes, models, and/or the like. For example, for a given piece of equipment, the equipment data store 408 may store maintenance guidelines, user manuals, standard specifications, normal operating parameters, testing instructions, and/or the like. This information may be provided to a mobile computing device 104 to assist in performing measurements. The facility data store 404 may include unique identifiers used to identify particular installations of equipment at a facility, and may refer to information stored in the equipment data store 408 to provide further description of the equipment.

One of ordinary skill in the art will recognize that the illustration of components as being present on the measurement processing server 102 is exemplary only, and that in some embodiments, components of measurement processing server 102 may instead be located on the mobile computing device 104, or split between the measurement processing server 102 and the mobile computing device 104.

Figure 5:
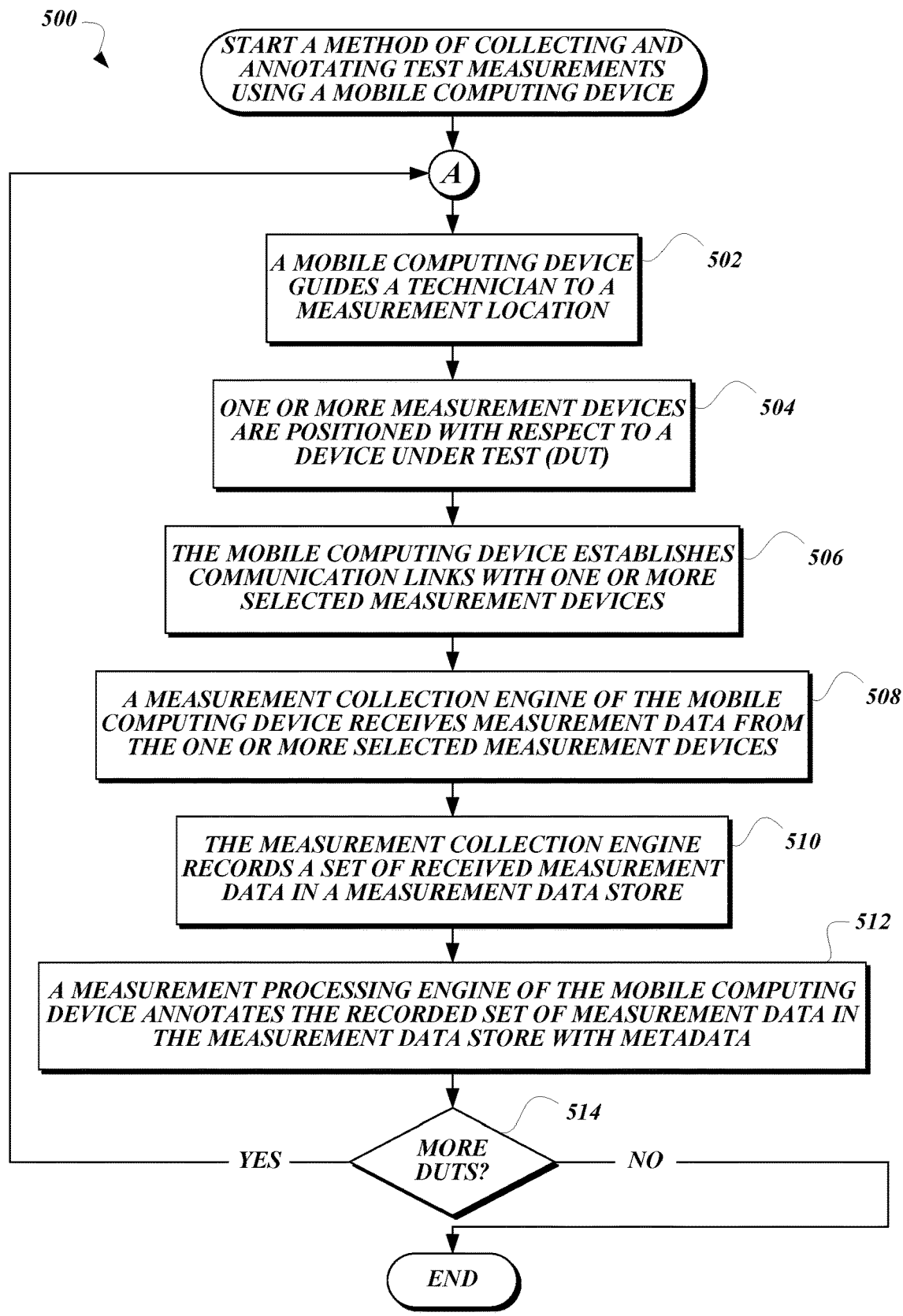
FIG. 5 is a flowchart that illustrates an exemplary embodiment of a method of collecting and annotating test measurements using a mobile computing device according to various aspects of the present disclosure.

FIG. 5 is a flowchart that illustrates an exemplary embodiment of a method 500 of collecting and annotating test measurements using a mobile computing device 104, according to various aspects of the present disclosure. From a start block, the method 500 proceeds to a continuation terminal ("terminal A"), and from terminal A to block 502, where a mobile computing device 104 guides a technician to a measurement location. Generally, a measurement location is a location at which a mobile computing device 104 can communicate with a measurement device 108 configured to measure properties of a device under test. In some embodiments, the measurement location may be in close proximity to the device under test, such that a handheld or other portable measurement device 108 may be placed in contact with the device under test or otherwise obtain measurement data from the device under test. In some embodiments, the measurement location may be in proximity to a network via which the mobile computing device 104 may communicate with a measurement device 108 configured to measure properties of a device under test at a different location. In some embodiments, the mobile computing device 104 may guide the technician to the measurement location by presenting a map, floor plan, or travel directions to the technician. In some embodiments, it may be assumed that the technician knows the location of the device under test, and the mobile computing device 104 may guide the technician to the measurement location by presenting a task list and an indication of the device to be tested.

Next, at block 504, one or more measurement devices 108 are positioned with respect to a device under test (DUT) 92, as illustrated in FIG. 1. For example, a sensor of the measurement device 108 may be placed in physical or electrical contact with the DUT 92 to detect a property such as vibration, voltage, resistance, and/or the like. As another example, a sensor of the measurement device 108 capable of sensing properties without being in physical contact with the DUT 92, such as a clamp meter, an infrared camera, and/or the like, may be positioned to sense a property of the DUT 92. One of ordinary skill in the art will recognize that, in some embodiments, the actions described in blocks 502 and 504 may be swapped in order, such as in embodiments where the measurement devices are left in position for monitoring the DUT 92 even between collections of measurements using a mobile computing device 104.

At block 506, the mobile computing device 104 establishes communication links with one or more selected measurement devices 108. The communication links may include transmission of data via a communication protocol or by any other technique discussed above or otherwise known to one of ordinary skill in the art. In some cases, the measurement devices 108 may initially operate in a mode in which the measurement devices 108 periodically communicate a signal indicating their presence, which the mobile computing device 104 can detect. The user may be required to initiate an input, such as press a button, on the measurement devices 108 or otherwise cause the measurement devices 108 to commence communicating such a presence detect signal. In any event, upon detection of the presence of one or more measurement devices 108, the mobile computing device 104 may display the availability of the measurement devices 108 to the user via the user interface 106.

The user may indicate to the mobile computing device 104 the particular measurement device 108 or devices that should be linked to the mobile computing device 104 for communication of measurement data. For example, in at least one implementation, the user may press particular buttons on the mobile computing device 104 that are associated with the available measurement devices 108. As another example, the user may touch particular text or icons on the user interface 106 presented on a touchscreen of the mobile computing device 104 to indicate a desire to link the mobile computing device 104 with the measurement devices 108. In response to such user indication, the mobile computing device 104 establishes communication links with the indicated measurement devices 108, e.g., by responding to the presence detect signal that is periodically sent by the measurement devices 108. The measurement devices 108 and the mobile computing device 104 may exchange configuration information that allows for exclusive or nonexclusive communication of measurement data from the measurement devices 108. In yet other embodiments, the mobile computing device 104 may automatically establish communication links with all measurement devices 108 that it detects.

Next, at block 508, a measurement collection engine 214 of the mobile computing device 104 receives measurement data from the one or more selected measurement devices 108. In some embodiments, the measurement data may be received via a network or wireless protocol of the communication link. In some embodiments, the measurement data may be received via other means. As nonlimiting examples, in some embodiments, the measurement data may be received by exchanging a tangible computer-readable medium between the mobile computing device 104 and a measurement device 108, by manual entry of the measurement data into the mobile computing device 104 by the technician, by capturing an image of the measurement device 108 using a camera of the mobile computing device 104, and/or using any other suitable technique. The measurement data may include a single value representing a property of the DUT 92 at a given time, or may include multiple values representing a time series of values representing a property of the DUT 92 over a period of time. At block 510, the measurement collection engine 214 records a set of received measurement data in a measurement data store 220. The set of received measurement data may include a single reading from a single sensor 330, multiple readings from a single sensor 330, or one or more readings from multiple sensors 330.

The method 500 then proceeds to block 512, where a measurement processing engine 216 of the mobile computing device 104 annotates the recorded set of measurement data in the measurement data store 220 with metadata. In some embodiments, the metadata used to annotate the recorded set of measurement data may include information describing when, where, and how the information was collected including, but not limited to: a timestamp; a GPS location (or a location obtained using other positioning technology) of the mobile computing device 104 and/or the measurement device 108; an equipment identifier that either uniquely identifies the DUT 92 or identifies a type or model of the DUT 92; an identifier of the measurement device 108; a record of settings of the measurement device 108; the particular test point or points on the DUT 92; a work order, task list, or job instruction that directed the collection of the measurement data; an identity of the technician collecting the measurement data; a text note; a voice note; an image; a video; an image annotation; and/or the like. In some instances, the DUT 92 may be labeled with human perceptible data, such as on a sticker, hang tag, or the like, that identifies the particular equipment. The technician may enter the equipment identity into the mobile computing device 104 based on the labeled data. In other instances, the DUT 92 may be labeled with a machine readable code, such as a barcode, a QR code, or a radio frequency identification (RFID) tag, that the technician can scan using the mobile computing device 104. Alternatively or in addition, the equipment identity and other information may be provided by a barcode or QR code printed on a work order delivered to the technician conducting the equipment measurements. The equipment identity corresponding to the scanned code can then be automatically stored in the metadata of the measurement data that is automatically being associated in a particular data group.

In some embodiments, the metadata used to annotate the recorded set of measurement data may include group identifying information. The group identifying information may associate the recorded set of measurement data with other recorded sets of measurement data, and this association may then be used to display or otherwise process the grouped sets measurement data together. In some embodiments, the group identifying information may include one or more group identifiers that may be automatically associated with the recorded set of measurement data. In at least one implementation, the mobile computing device 104 may associate measurement data into a group based on an element that is common to the metadata of each received data measurement, such as time information that reflects when the data was measured. For example, measurement data that is captured simultaneously or near in time to each other, such as within a predetermined amount of time of each other, from various measurement devices 108 may automatically be grouped into a single data group, and the data group may be associated with a particular test point or group of test points of the DUT 92. The identity of the test point or group of test points may be supplied by the user, either before, during, or after receipt of the measurement data. In other implementations, the identity of the test point or group of test points may automatically be obtained from the DUT 92, from the measurement devices 108, or from the mobile computing device 104 or other devices. For example, a GPS circuit in a measurement device 108 may provide location data that can be included with or otherwise associated with the measurement data being transmitted to the mobile computing device 104. In some cases, the location data may be associated in a memory or other storage device with one or more test points. The location data may be used (e.g., as an index or keyword for look up in a table) to identify particular test points associated with the location, either in the measurement devices 108 or in the mobile computing device 104.

For example, multiple sets of measurement data taken with different measurement devices 108 of the same DUT 92 (such as visual images, infrared images, and/or thermal images captured by a camera or thermal imager, electrical measurements such as voltage, current, or impedance measurements captured by a DMM, and measurement of mechanical parameters such as vibration or pressure captured by portable sensors, and/or the like) obtained at substantially the same time (such as, for example, within a few seconds or minutes of each other) may be grouped together to be displayed and/or analyzed as part of a single test. Said grouping may also be based on group identifying information specified by the technician or on some other piece of common metadata other than the timestamp. For example, measurement data captured within a predetermined distance of each other as determined by a positioning system may be grouped together.

As another example, sets of measurement data taken of different DUTs 92 that are the same type of equipment (such as, for example, two different units of the same model of a motor) may be grouped together to provide comparisons between multiple separate units. The mobile computing device 104 may also be configured to receive text, capture an image, or record audio or video initiated by the technician, such as a voice comment or text annotation of measurement data or as a recording of equipment appearance or sound, and associate such text, image, or audio/video recordings with the measurement data in a particular group. As yet another example, a technician may provide commentary on observations of the DUT 92 at the time the measurement data is obtained. Such commentary may be received from the technician before, during, or after the data measurements occur. By saving the user-initiated text or audio/video recordings with metadata that is held in common with the measurement data, the text or audio/video recordings may likewise be associated in the same group with the measurement data.

A feature of the present disclosure is that group identifying information may be generated either before, during, or after the measurement data is obtained. In instances where measurement data is captured before the group identifying information is generated, the measurement data may automatically be associated in a group according to parameters such as the time or location when the data is measured or transmitted.

Automatically generated groups may be presented to the technician with a prompt for the technician to confirm the automatically generated information or to supply further group identifying information. The technician can input information pertaining to the group and have the information stored in the metadata. For example, the technician may enter information regarding the measured equipment and have the identity of the equipment stored with the measurement data in the group. In some embodiments, the technician manually inputs the identity of the measured equipment. In other embodiments, the mobile computing device 104 may display a list of previously identified equipment and allow the technician to select the equipment being measured. If the equipment being measured is not included in the displayed list, the technician may initiate a prompt on the mobile computing device 104 that allows the technician to create a new equipment identity and store the equipment identity in the list for later retrieval when the equipment is again being measured. In yet other embodiments, the mobile computing device 104 may receive or sense location data (e.g., through a GPS reading or other positioning technology) and automatically provide a list of known equipment associated with the location data, from which the technician can select the equipment record matching the DUT 92. In still other embodiments, the mobile computing device 104 may automatically generate a group based on work order data, either by grouping all measurements gathered while processing a work order, by obtaining equipment identifiers using the work order data, and/or using any other suitable technique.

Next, the method 500 proceeds to a decision block 514, where a determination is made regarding whether more devices remain to be tested. If the result of the determination at decision block 514 is YES, the method 500 proceeds to terminal A, and the actions discussed with respect to blocks 502 through 514 are repeated for the next device to be tested. Otherwise, if the result of the determination at decision block 514 is NO, the method 500 proceeds to an end block and terminates.

In various embodiments, data groups that have been generated by the mobile computing device 104 may be presented to the user in a variety of formats for viewing, analyzing, and reporting. For example, a textual description of a data group or a visual graph of measurement data in the data group may be shown to the user. In instances where a data group includes a large amount of measurement data, the user may be presented with a small portion or short description of the measurement data with a prompt that the user may select to receive additional detail regarding the data measurements in the group. If desired, the user may divide the measurement data in a data group into two or more smaller data groups. Information that distinguishes the two or more smaller groups is stored in the metadata of the data measurements pertaining to the smaller groups.

By automatically associating data into data groups, an improved process is provided for easily organizing and presenting the measurement data to the user in a clear, straightforward, and visual manner. The measurement data is packaged and/or formatted in a way that makes it easy for the user and others to analyze the data in the different data groups and evaluate the status of the equipment being measured.

In some embodiments, the system 100 disclosed herein may be particularly useful for large organizations that have a desire to monitor or otherwise measure a large number of units of equipment, or to monitor or otherwise measure a large number of properties of a given unit of equipment. Accordingly, some embodiments of the present disclosure further provide a unified data collection and reporting interface for equipment being measured. These embodiments include processes for collecting data from disparate measurement devices positioned to obtain measurements of equipment in one or more locations, storing the measurement data in one or more associated data structures, and reporting the measurement data in a unified display.

One example of a unified display is a single, scrollable "equipment page" presented by the user interface engine 212 that is associated with particular equipment and provides a view of the measurement data captured and/or processed with regard to the equipment. By storing and displaying disparate data collected with regard to a given unit or type of equipment on a single page, a user is able to evaluate both historical data and presently measured data, observe trends in the data, determine the status of the equipment, and predict future maintenance needs of the equipment. Such analysis may be conducted by a technician on site with the equipment or by management personnel and/or experts at remote locations that have access to the unified data collection and reporting interface for the equipment.

In some cases, it may be helpful to a user to compare the measurement data of particular equipment to the measurement data of similar equipment in other locations, particularly if the health status of the other equipment has already been established. Equipment pages for installations of similar equipment may be displayed in a manner (e.g., side-by side or picture-in-picture) that facilitates comparison of the measurement data obtained from a DUT 92 to overall trends shown in other installations of similar equipment. Comparing the DUT 92 with similar equipment in other locations may facilitate evaluation of a health status of the DUT 92.

Figure 6:
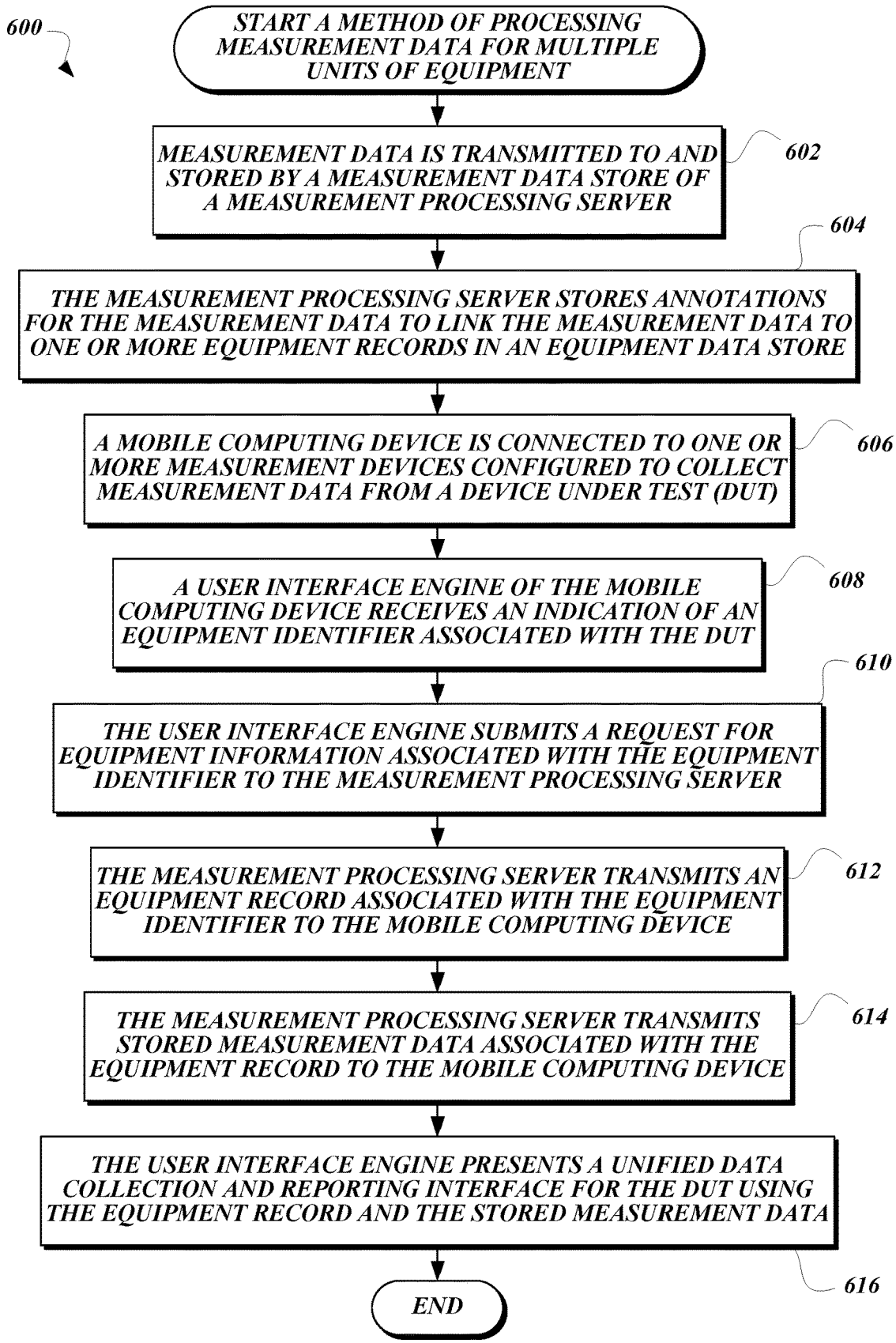
FIG. 6 is a flowchart that illustrates an exemplary method of processing measurement data for multiple units of equipment to generate a unified data collection and reporting interface according to various aspects of the present disclosure.

FIG. 6 is a flowchart that illustrates an exemplary method 600 of processing measurement data for multiple units of equipment to generate a unified data collection and reporting interface according to various aspects of the present disclosure. From a start block, the method 600 proceeds to block 602, where measurement data is transmitted to and stored by a measurement data store 406 of a measurement processing server 102. The measurement data stored in block 602 represents measurements collected from one or more units of equipment. In some embodiments, the measurement data may have been collected using a method similar to the method illustrated in FIG. 5 and discussed above, though in other embodiments, any other suitable method may be used to obtain the measurement data. Next, at block 604, the measurement processing server 102 stores annotations for the measurement data to link the measurement data to one or more equipment records in an equipment data store 408. In some embodiments, the annotation that links the measurement data to one or more equipment records may be an equipment identifier that uniquely identifies an equipment record in the equipment data store 408, and may be added along with the rest of the metadata stored with the measurement data. One of ordinary skill in the art may consider the actions described above in blocks 602-604 as providing the system 100 with historical measurement data for use in creating the unified data collection and reporting interface as described below.

Once the system 100 has obtained some historical measurement data for equipment to be compared to the DUT 92, a unified data collection and reporting interface may be generated by the system 100. Accordingly, the method 600 proceeds to block 606, where a mobile computing device 104 is connected to one or more measurement devices 108 configured to collect measurement data from one or more DUT 92, as described above. Next, at block 608, a user interface engine 212 of the mobile computing device 104 receives an indication of an equipment identifier associated with the DUT 92. The equipment identifier may be provided in a human-perceptible form on a name plate, hang tag, sticker, label, and/or the like attached to the DUT 92. In some embodiments, the equipment identifier may be entered into the mobile computing device 104 by manual entry, by scanning of text on the DUT 92, by scanning a bar code or QR code label, and/or by any other suitable technique, similar to the techniques discussed above. Meanwhile, in other embodiments, the equipment identifier may be determined by the technician selecting equipment matching the DUT 92 from the unified data collection and reporting interface presented by the user interface engine 212.

Production plants, factories, facilities, etc., typically have multiple installations of equipment of a given type at different locations. The unified data collection and reporting interfaces for different equipment installations may be organized in the mobile device and in remote data processing centers to enable a technician to quickly identify and select particular equipment for viewing of the corresponding interface. In various embodiments, attributes such as equipment name, type, location, and status may be used to distinguish different installations of equipment. The unified data collection and reporting interfaces for the different equipment installations may include such equipment attributes. The equipment attributes may be displayed to facilitate user identification and selection of a desired installation of equipment.

For example, the location of equipment may be identified by a textual description of the equipment's surroundings. Alternatively or in addition, graphical depictions illustrating the location of the equipment relative to its surroundings may be provided. For example, a map showing a floor plan of a factory or facility having multiple equipment installations may be shown with icons representing particular equipment installations within the factory or facility. The icons may be positioned within an image of the floor plan to illustrate the respective locations of the equipment. In instances where the map is larger than the available area on the display, the depiction of the map may be scrollable in one or more dimensions to enable easy access to the complete floor plan map.

In some embodiments, the map may be a formal illustration of a floor plan. In other embodiments, the map may be a hand drawn sketch generated by a technician and saved in the unified data collection and reporting interface for the equipment. The image of the floor plan may be, for example, a photograph of a sketch or formal illustration on paper, or it may be a sketch drawn directly onto the screen of the display. Images of the equipment stored in the unified data collection and reporting interface for the equipment may further facilitate identification of the particular equipment. Depicting a floor plan map or other graphical image of equipment surroundings may help a technician to physically find particular equipment. Accordingly, a technician sent to measure data with regard to particular equipment may be guided when attempting to locate the equipment on site.

In some embodiments, the map data may include GPS or other positioning information. In such embodiments, a mobile computing device 104 capable of receiving or generating GPS data may superimpose an icon onto a depiction of the map indicating the position of the mobile computing device 104 relative to equipment and other surroundings in the map. Such depictions may further guide a technician sent to measure data with regard to particular equipment.

A technician may also use map data to identify particular equipment that the technician is seeking to evaluate. For example, in at least one embodiment, a graphical map may be displayed to the technician showing various equipment installations. The technician can then touch or click a mapped location on the display to select particular equipment at that location. Selection of the particular equipment causes the equipment identifier for that equipment to be selected.

Alternatively or in addition to graphically depicting a map showing equipment installations, a mobile computing device 104 may display a listing of building areas or room types (potentially organized in a hierarchy) that enables a technician to identify and select particular equipment for evaluation. An exemplary embodiment may provide a list of building areas, such as basement, floor, wall, or roof, that are associated with the locations of different equipment. Upon selection of a building area, the mobile computing device 104 may further display a more detailed list of rooms or locations within the selected building area. Upon selection of a room or location within the building area, the technician may then be provided a listing of equipment in the selected room or location. Eventually, the technician is able to identify and select particular equipment based on its relative location in the building, and thereby select the equipment identifier to be used.

Another exemplary embodiment may provide a listing of room types, such as boiler room, machine room, assembly floor, laboratory, office, and/or the like, where equipment is located. Upon selection of a room type, the mobile computing device 104 may further display a more detailed list of rooms that match the selected room type. Thereafter, upon selection of a particular room, the technician may be provided a listing of equipment in the selected room. The technician may then identify and select particular equipment from the list. Selection of particular equipment from the list causes the equipment identifier for that equipment to be used. In some embodiments, the map information, the locations of equipment, and/or the like may be stored in the facility data store 404 and obtained therefrom by the mobile computing device 104.

Once the equipment identifier is obtained, the method 600 proceeds to block 610, where the user interface engine 212 submits a request for equipment information associated with the equipment identifier to the measurement processing server 102. At block 612, the measurement processing server 102 transmits an equipment record associated with the equipment identifier to the mobile computing device 104.

At block 614, the measurement processing server 102 transmits stored measurement data associated with the equipment record to the mobile computing device 104. Once the mobile computing device 104 has received the stored measurement data and/or the equipment record, the method 600 proceeds to block 616, where the user interface engine 212 presents a unified data collection and reporting interface for the DUT 92 using the equipment record and the stored measurement data.

In various embodiments, the unified data collection and reporting interface for particular equipment may be configured to present reference documents stored in the equipment record that are helpful to the technician and others. For example, the equipment record may hold safety manuals or maintenance guidelines that the technician and others can access while operating the equipment, making measurements, or evaluating measurement data. In addition, work orders pertaining to the equipment and subsequent reports may be stored in the equipment record for later access.

In various embodiments, the unified data collection and reporting interface for particular equipment may also be configured to present the stored measurement data, either by itself or side-by-side with a current measurement value. For example, the interface may present a graph that shows trends in a measurement value over time for a given DUT 92, or for all similar measurement values collected from equipment of the same equipment type, and may also present the current measurement value for comparison. In various embodiments, the interface for particular equipment may also include features such as a status bar that quickly illustrates the current status of the equipment. For example, a green status bar may indicate equipment in good maintenance condition, while a yellow or red status bar may indicate equipment needing further attention. The status may be updated by a technician, or may be automatically determined by comparing a current measurement value or values to the stored measurement data or to acceptable values stored in the equipment record. The interface may include images of the equipment taken before, during, or after measurement data is obtained. Images of the equipment obtained over time may be compared to identify changes indicative of future maintenance needs. If desired, a tool may be provided in which a previously obtained image of the equipment is superimposed on an image to be taken or presented side-by-side with an image to be taken, allowing the technician to align the two images, which facilitates later comparison of the images. In some embodiments, the tool may also provide the ability to compare two previously obtained images for comparison to each other, either in a side-by-side presentation or superimposed on one another. In some embodiments, the tool may provide the ability to provide a side-by-side or superimposed comparison of images of different units of equipment. The interface may include collections of measurement data organized into groups as described above. A technician viewing the equipment page for particular equipment may select one or more of the data groups for further viewing and analysis.

When providing measurement data for viewing and analysis, the unified data collection and reporting interface may automatically provide graphs of the measurement data collected over time. Alternatively or in addition, data captured at a particular instance of time may be displayed as a static numerical value. Image data stored in the measurement data store 406 or equipment data store 408 may be displayed as images in the interface. Such images may be shown along with graphs and/or static numerical values of other measurement data to enable a broader, holistic view of the equipment. As will be understood by one of ordinary skill in the art, when image data is discussed herein, said image data may include visible light image data, infrared image data, or any other suitable type of image data whether in a visible light spectrum or not.

Once the user has finished interacting with the unified data collection and reporting interface, the method 600 proceeds to an end block and terminates.

In some embodiments, the system 100 may be configurable to automatically generate reports in formats other than the unified data collection and reporting interface as well. For example, in some embodiments the mobile computing device 104, the measurement processing server 102, or some other computing device associated with the system 100 may include a report definition. The report definition may include measurements to be reported in a particular format, such as a regulatory form and/or the like. Upon collection of measurements to be entered in the form, the system 100 may automatically generate a report in the format indicated in the report definition, and may provide the report for submission to a regulatory agency, for storage in a record associated with the DUT, and/or the like.

The present disclosure further provides automated processes for providing a combined display of measurement data that represents related parts of a combined measurement. In some cases, the combined measurement may be a multiphase parameter and the related parts of the combined measurement are the component phases of the multiphase parameter. A multiphase parameter may comprise multiple components that differ from one another according to a phase of the respective component. One example of a multiphase parameter is three-phase power in a three-phase power system.

As discussed above, in one example the mobile computing device 104 may receive measurement data from a plurality of current-sensing and/or voltage-sensing measurement devices 108 and establish communication connections with each of the measurement devices 108. The mobile computing device 104 may receive the measurement data from the measurement devices 108 during an overlapping time interval, as recognized by a timestamp or other time information associated with the measurement data indicating when the measurement data was generated by the measurement devices 108 and/or received by the mobile computing device 104. Such time information may indicate a time proximity when the measurement data was generated by the measurement devices 108. In view of this time information, the mobile computing device 104 may automatically associate, or group together, such measurement data as discussed above in greater detail.

In accordance with the present disclosure, the mobile computing device 104 may further consider such time information indicative of the measurement data representing related parts of a combined measurement and automatically display the grouped measurement data in a combined display of the measurement data that shares at least one axis of measurement. In at least one embodiment, the combined display may be a graph depicting the measurement data sharing at least one axis of measurement. Typical axes of measurement are time and magnitude.

For example, the mobile computing device 104 may establish communication connections with three current-sensing or three voltage-sensing measurement devices 108 and simultaneously receive measurement data from the measurement devices. Based on time information associated with the measurement data, the mobile computing device 104 may not only group the measurement data together but interpret the measurement data as representing component parts of a three-phase power signal, where the measurement data from each measurement device 108 represents a particular phase of the power signal.

Instead of displaying three separate graphs of the measurement data (i.e., a separate graph with separate axes of measurement for the measurement data from each of the three measurement devices), as may be done with conventional systems, the mobile computing device 104 of the present disclosure is configured to automatically generate and present a single graph displaying the current or voltage measurements of the three phases together, without requiring user input to cause preparation of such a graph. In some cases, the combined display of the measurement data may share at least two axes of measurement. In cases where the combined display provides a graph of the measurement data, the display of each set of measurement data may be superimposed on one another in the graph using, for example, magnitude and time as the shared axes of measurement. By superimposing the measurement data in a combined graph with at least two shared axes of measurement, the magnitude and phase relationships between the different components of the multiphase parameter are more easily observed.

As another example of a combined measurement, the mobile computing device 104 may receive multiple temperature measurements from measurement devices 108 placed in an HVAC system. The measurement devices 108 may be configured to measure the temperature of different parts of the HVAC system, such as the burner, flue, or air duct, etc. By receiving and evaluating the measurement data from the measurement devices 108 in a combined display as discussed above, a user of the mobile computing device 104 may assess the health of the HVAC system by looking at relationships between the multiple temperature measurements. For example, one may expect the flue temperature of the HVAC system to track with changes in the boiler temperature. A too-rapid rise in the air duct temperature after a rise in the burner temperature may indicate a crack in the heat exchanger, while a too-slow rise in the air duct temperature might indicate a blockage. By automatically grouping the multiple temperature measurements together as a combined measurement for the HVAC system, the health of the HVAC system may be more easily assessed. Similar considerations may be given to other systems in which multiple measurements of equipment in the systems may be considered related parts of a combined measurement and the measurement data may be automatically grouped together for a combined display, in accordance with the present disclosure.

Figure 7:
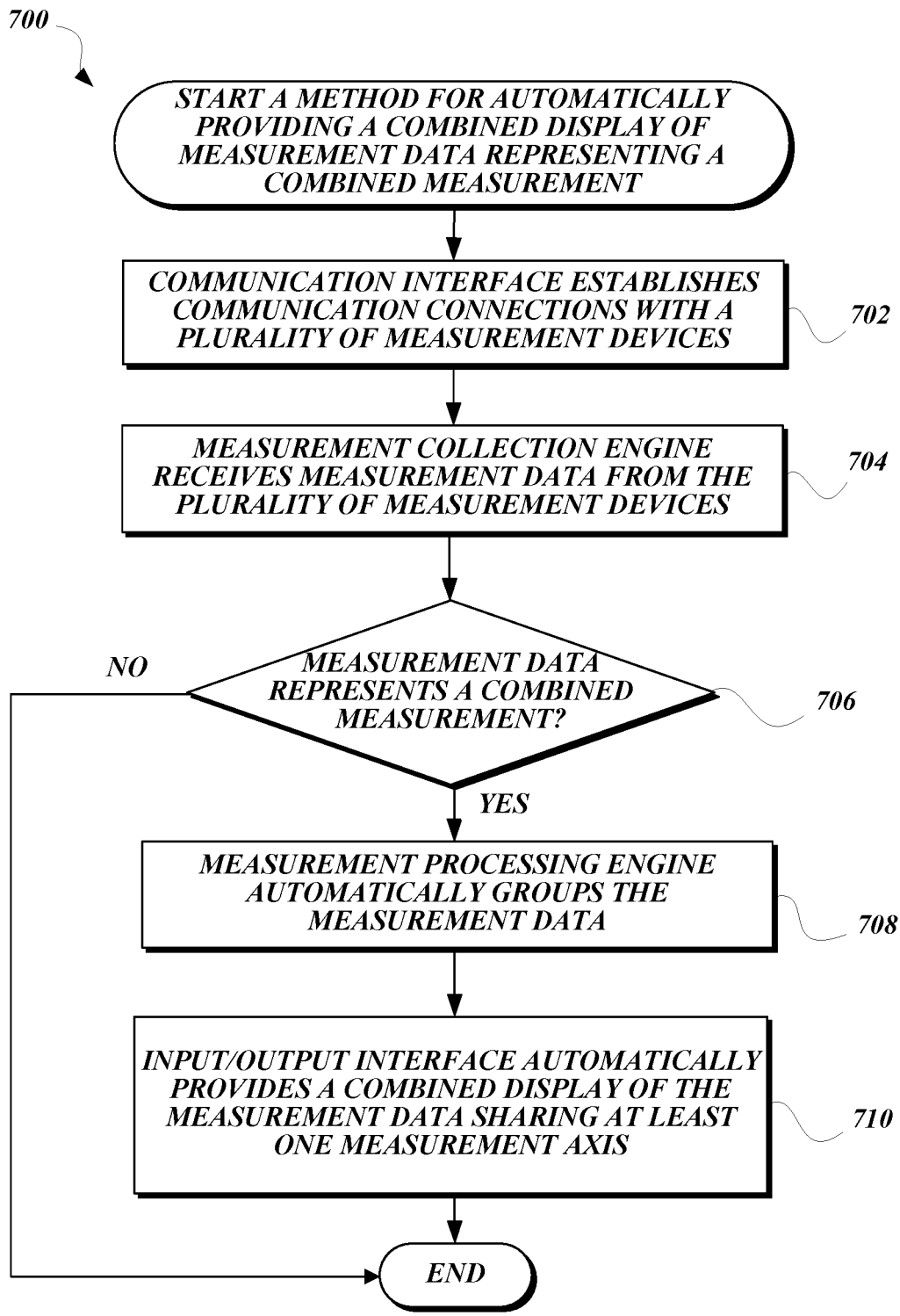
FIG. 7 is a flowchart that illustrates an exemplary method for automatically generating a combined display of measurement data representing a combined measurement.

FIG. 7 is a flowchart that illustrates an exemplary method 700 for automatically generating a combined display of measurement data representing a combined measurement. As a first step at block 702, the communication interface 224 of a mobile computing device 104 establishes communication connections with a plurality of measurement devices 108. Next, at block 704, a measurement collection engine 214 of the mobile computing device 104 receives measurement data from the plurality of measurement devices. At this point, the mobile computing device 104 is configured to evaluate available information that may indicate that the measurement data represents related parts of a combined measurement, as indicated at decision block 706.

As one example described above, information indicative of the measurement data representing related parts of a combined measurement may include time information indicating proximity of time when the measurement data was generated by the plurality of measurement devices. In particular, the time information may indicate that the measurement data was generated by the measurement devices during an overlapping time interval. Simultaneous generation of measurement data by multiple measurement devices, particularly when measuring the same parameter, may be interpreted as indicating a combined measurement, such as a measurement of a multiphase parameter.

As another example, information indicative of the measurement data representing related parts of a combined measurement may include location information indicating proximity of location where the measurement data was generated by the plurality of measurement devices. In particular, the location information may indicate that the measurement data was generated by the measurement devices at an equipment test point. The mobile computing device may automatically interpret the proximity of location of the measurement devices as measuring the same test point of the equipment, wherein each measurement device is sensing a related part of the combined measurement, such as a particular phase of a multiphase parameter.

In contrast to conventional systems that display different sets of measurement data in separate graphs and require careful manipulation of the data by a user in order to join the different sets of measurement data into a single graph, the present disclosure provides a method, system, and computer-readable medium in which a combined display of measurement data representing a combined measurement is automatically presented in a combined display. In some embodiments, the combined display may be a graph that graphically depicts the measurement data. In other embodiments, the combined display may be a numerical or other non-graphical display. In any event, a combined display advantageously facilitates faster evaluation of the measurement data when the measurement data represents a combined measurement, such as a multiphase parameter.

For example, in a three-phase power system as described above, the mobile computing device 104 of the present disclosure can detect receipt of multiple current or voltage measurements and interpret the current or voltage measurements as representing measurements of the same test point of a three-phase power system. Accordingly, the mobile computing device 104, or other computing device in the system, can automatically produce a combined display of the three-phase measurement data as discussed above.

A user desiring to measure and evaluate the different phases of a three-phase power system need only position the three current or voltage measurement devices 108 with regard to the component parts of the three-phase power system being measured and establish communication connections between the mobile computing device 104 and the measurement devices 108. The mobile computing device 104 receives the measurement data from the measurement devices 108 and, as described above, automatically generates and presents a combined display, such as a graph providing a graphical depiction of the three different phases. This is particularly useful, for example, when the user desires to quickly evaluate whether a load placed on a three-phase power system is balanced.

Returning to FIG. 7, if the mobile computing device 104 determines that the measurement data represents related parts of a combined measurement, the measurement processing engine 216 of the mobile computing device 104 automatically groups the measurement data, as indicated at block 708. The grouped measurement data is then processed and provided to the input/output interface 222 as indicated at block 710, for automatically displaying the grouped measurement data in a combined display that shares at least one axis of measurement, as described above.

While embodiments of systems and methods have been illustrated and described in the foregoing description, it will be appreciated that various changes can be made therein without departing from the spirit and scope of the present disclosure. For example, while embodiments of the mobile computing device have been described in the context of a smart phone executing one or more programmed applications, other embodiments of the mobile computing device may include a handheld measurement tool that is additionally capable of measuring properties of equipment. The measurement devices, as indicated earlier, may include handheld measurement tools as well as multipurpose and single use sensors that are positioned relative to equipment to be measured. Computer-executable instructions that cause one or more computing devices to perform processes as described herein may be stored in a nontransitory computer readable medium accessible to the one or more computing devices. Moreover, it should be understood that rearrangement of structure or steps in the devices or processes described herein that yield similar results are considered within the scope of the present disclosure. Accordingly, the scope of the present disclosure is not constrained by the precise forms that are illustrated for purposes of exemplifying embodiments of the disclosed subject matter.

The embodiments of the invention in which an exclusive property or privilege is claimed are defined as follows:

1. A computer-implemented method for automatically generating a combined display of measurement data, the method comprising:
   establishing, by a mobile computing device, communication connections with a plurality of measurement devices configured to measure electrical or mechanical properties of equipment and generate measurement data based on the electrical or mechanical properties of the equipment;
   receiving, by the mobile computing device, the measurement data generated by the plurality of measurement devices;
   after receiving the measurement data, determining whether the measurement data represents related parts of a combined measurement, wherein said determining whether the measurement data represents related parts of a combined measurement is based on location information indicating a proximity of respective physical locations of the plurality of measurement devices; and
   in response to determining that the measurement data represents related parts of a combined measurement:
      automatically grouping the measurement data that was determined to represent related parts of a combined measurement to produce grouped measurement data; and
      automatically displaying the grouped measurement data in a combined display of in which the grouped measurement data, as displayed, shares at least one axis of measurement.

2. The method of claim 1, wherein the combined measurement is a multiphase parameter, and the measurement data received from each measurement device represents a phase of the multiphase parameter.

3. The method of claim 2, wherein the multiphase parameter is an electrical parameter having at least three component phases.

4. The method of claim 3, wherein the combined display includes three component phases of a three-phase voltage, current, or power parameter, and wherein the at least one axis of measurement represents time.

5. The method of claim 1, wherein determining whether the measurement data represents related parts of a combined measurement is further based on time information indicating a proximity of time when the measurement data was generated by the plurality of measurement devices.

6. The method of claim 5, wherein the time information indicates that the measurement data was generated by the plurality of measurement devices during an overlapping time interval.

7. The method of claim 1, wherein the location information indicates a proximity of location where the measurement data was generated by the plurality of measurement devices.

8. The method of claim 7, wherein the location information indicates that the measurement data was generated by the plurality of measurement devices at an equipment test point.

9. The method of claim 1, wherein the grouped measurement data, as displayed in the combined display, shares at least two axes of measurement.

10. The method of claim 9, wherein the combined display is a graph of the grouped measurement data, and wherein the grouped measurement data is superimposed in the graph using the at least two axes of measurement.

11. A system for automatically generating a combined display of measurement data, the system comprising:
    a mobile computing device configured to:
       establish communication connections with a plurality of measurement devices configured to measure electrical or mechanical properties of equipment and generate measurement data based on the electrical or mechanical properties of the equipment;
       receive the measurement data generated by the plurality of measurement devices;
       after receiving the measurement data, determine whether the measurement data represents related parts of a combined measurement, wherein the measurement data is determined to represent related parts of a combined measurement based on location information indicating a proximity of respective physical locations of the plurality of measurement devices; and
       in response to determining that the measurement data represents related parts of a combined measurement:
          automatically group the measurement data that was determined to represent related parts of a combined measurement to produce grouped measurement data; and
          automatically display the grouped measurement data in a combined display in which the grouped measurement data, as displayed, shares at least one axis of measurement.

12. The system of claim 11, wherein the combined measurement is a multiphase parameter, and the measurement data received from each measurement device represents a phase of the multiphase parameter.

13. The system of claim 12, wherein the multiphase parameter is an electrical parameter having at least three component phases.

14. The system of claim 13, wherein the combined display includes three component phases of a three-phase voltage, current, or power parameter, and wherein the at least one axis of measurement represents time.

15. The system of claim 11, wherein the mobile computing device is further configured to determine whether the measurement data represents related parts of a combined measurement based on time information indicating a proximity of time when the measurement data was generated by the plurality of measurement devices.

16. The system of claim 15, wherein the time information indicates that the measurement data was generated by the plurality of measurement devices during an overlapping time interval.

17. The system of claim 11, wherein the location information indicates a proximity of location where the measurement data was generated by the plurality of measurement devices.

18. The system of claim 17, wherein the location information indicates that the measurement data was generated by the plurality of measurement devices at an equipment test point.

19. The system of claim 11, wherein the grouped measurement data, as displayed in the combined display, shares at least two axes of measurement.

20. The system of claim 19, wherein the combined display is a graph of the grouped measurement data, and wherein the grouped measurement data is superimposed in the graph using the at least two axes of measurement.

* * * * *